US005786182A

United States Patent [19]

Catanzariti et al.

[11] Patent Number: 5,786,182

[45] Date of Patent: Jul. 28, 1998

[54] DUAL CHAMBER DISPOSABLE REACTION VESSEL FOR AMPLIFICATION REACTIONS, REACTION PROCESSING STATION THEREFOR, AND METHODS OF USE

[75] Inventors: Luigi Catanzariti, Duxbury; Bryan W. Kluttz, Norwell; Geoff A. McKinley, Duxbury; Arthur L. Garland, Carver; Louis Graziano, Rockland; James G. Moe, Franklin; Marcela Vera-Garcia, Framingham, all of Mass.; James Clement Bishop, Columbia, Mo.; David Chastain, Acton, Mass.; Fabio Gennari, Florence, Italy

[73] Assignee: bioMérieux Vitek, Inc., Hazelwood, Mo.

[21] Appl. No.: 850,207

[22] Filed: May 2, 1997

[51] Int. Cl.[6] .............................. C12P 19/34; C12M 3/00; G01N 21/00; C12N 15/00

[52] U.S. Cl. ........................ 435/91.1; 435/91.2; 435/91.5; 435/285.1; 435/287.2; 435/287.3; 435/287.6; 435/287.9; 435/288.2; 435/288.5; 435/286.1; 422/64; 422/101; 422/102; 935/78; 935/87; 935/88

[58] Field of Search .................................. 435/91.1, 91.2, 435/91.5, 285.1, 287.3, 287.6, 287.9, 288.2, 288.5, 286.1, 287.2; 422/64, 101, 102; 935/78, 87, 88

[56] References Cited

U.S. PATENT DOCUMENTS

| | | | |
|---|---|---|---|
| 4,956,148 | 9/1990 | Grandone | 422/64 |
| 5,324,481 | 6/1994 | Dunn et al. | 422/64 |
| 5,437,990 | 8/1995 | Burg et al. | 435/91.2 |
| 5,498,392 | 3/1996 | Wilding et al. | 422/68.1 |
| 5,510,084 | 4/1996 | Cros et al. | 422/104 |
| 5,554,516 | 9/1996 | Kacian et al. | 435/91.21 |
| 5,587,128 | 12/1996 | Wilding et al. | 422/50 |
| 5,645,801 | 7/1997 | Bouma et al. | 422/68.1 |

OTHER PUBLICATIONS

Mini VIDAS Operators Manual, bioMérieux Vitek, Inc. (1995).

Brochure materials, VIDAS automated immunoanalyzer system, bioMérieux Vitek, Inc. (1994).

Mini VIDAS automated immunoanalyzer system of bioMérieux Vitek, Inc. (see Mini VIDAS Operators Manual).

VIDAS test strip for use in VIDAS system, available from bioMérieux Vitek, Inc. (see pp. 3–17 of Mini Vidas Operators Manual).

*Primary Examiner*—David A. Redding

*Attorney, Agent, or Firm*—McDonnell Boehnen Hulbert & Berghoff

[57] ABSTRACT

A reaction vessel for a nucleic acid amplification reaction has a first chamber containing an amplification reagent mix, a second chamber containing an amplification enzyme, and a fluid channel or chamber connecting the first and second chambers together. A fluid sample is introduced into the first chamber. After a denaturation and primer annealing process has occurred in the first chamber, the fluid channel is opened to allow the solution of the reagent and fluid sample to flow into the second chamber. The second chamber is maintained at an optimal temperature for the amplification reaction.

A station is described for processing test strips incorporating the reaction vessels. The station includes temperature and vacuum control subsystems to maintain proper temperatures in the reaction vessel and effectuate the transfer of the fluid from one chamber to the other in an automated fashion without human intervention.

25 Claims, 23 Drawing Sheets

FIG.10
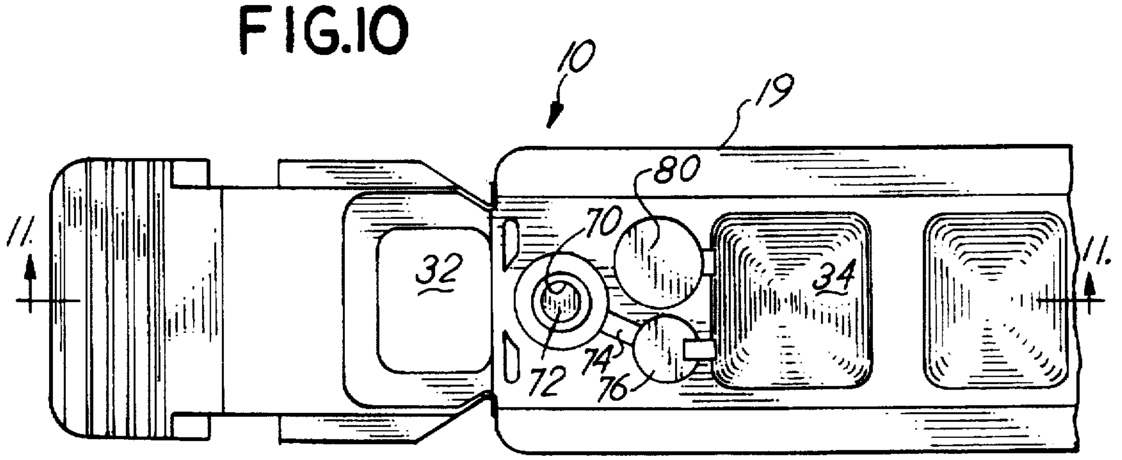
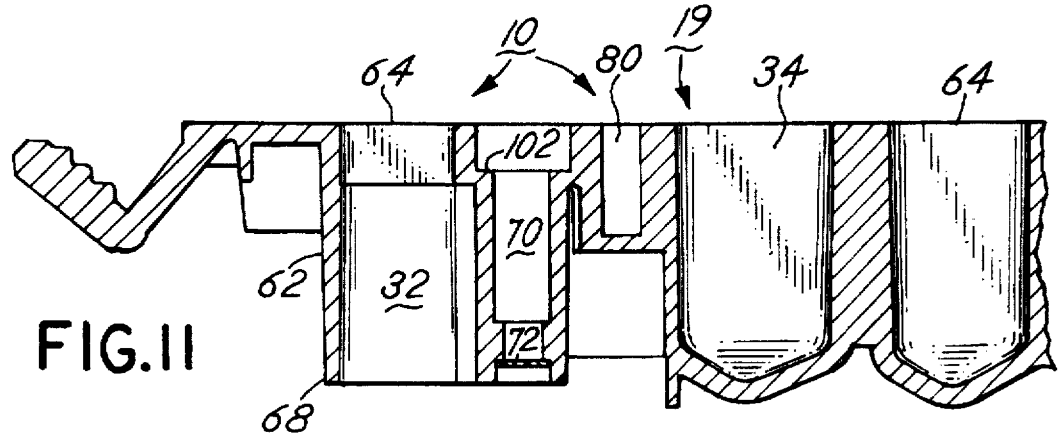
FIG.11
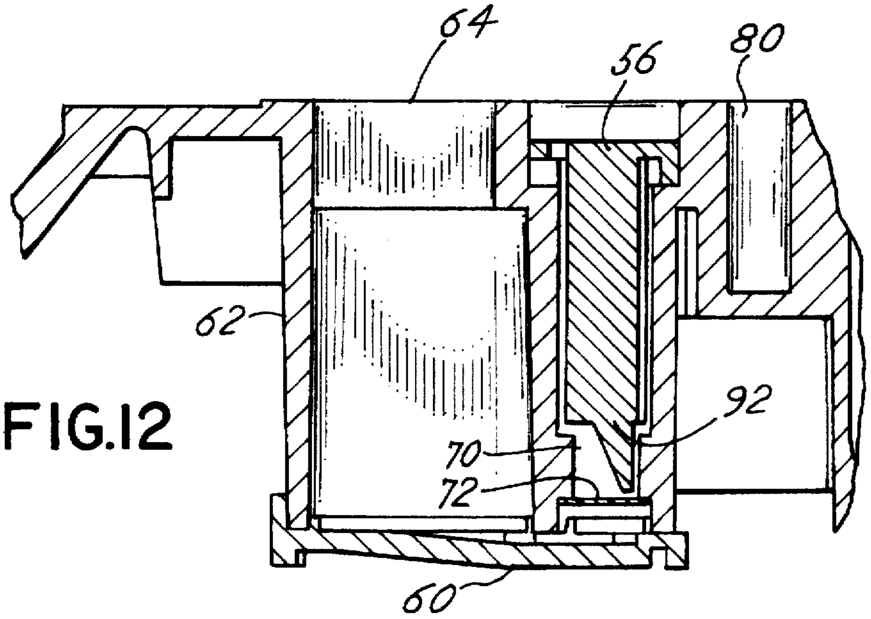
FIG.12

FIG.13
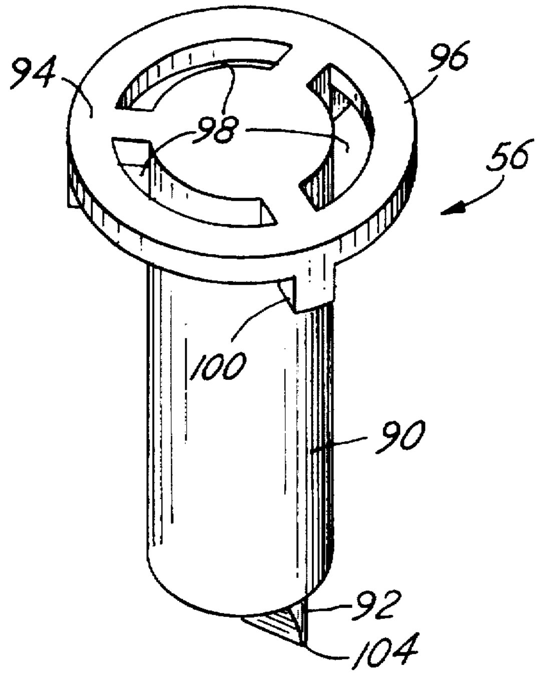
FIG.14
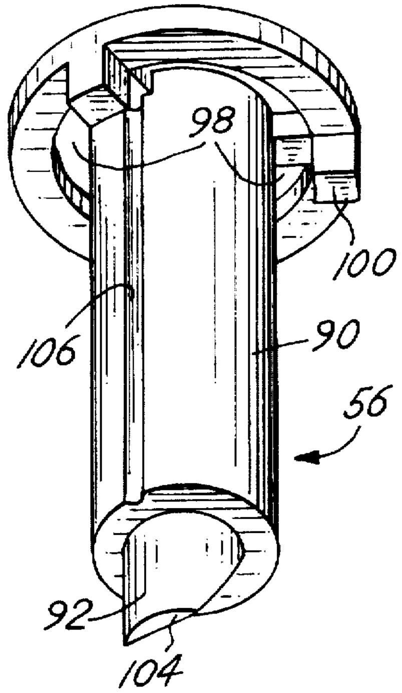
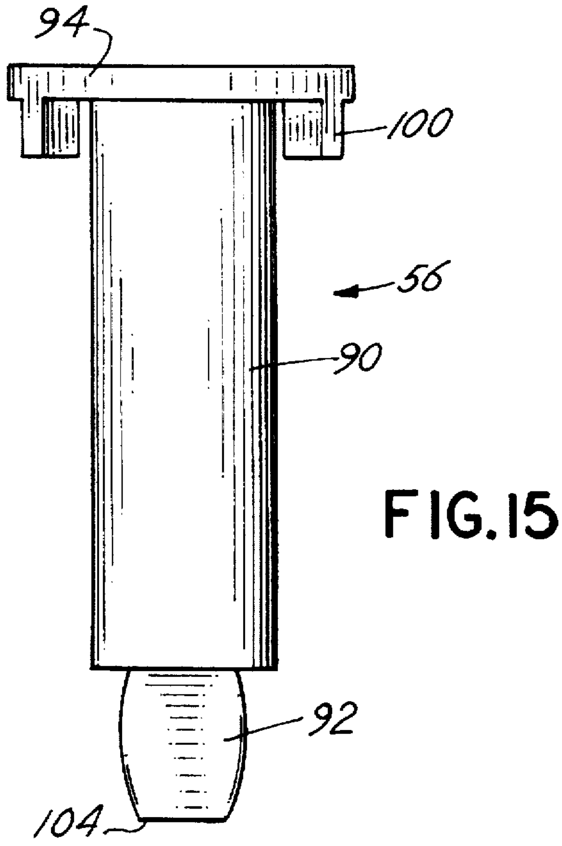
FIG.15

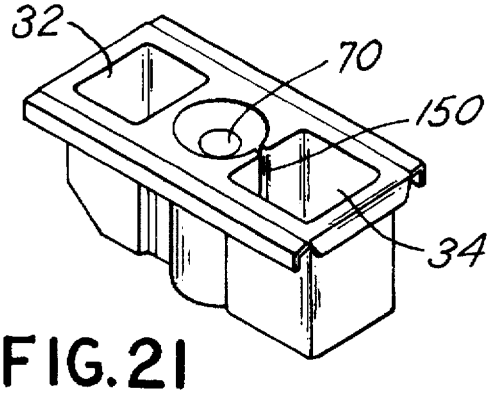
FIG. 21
FIG. 24
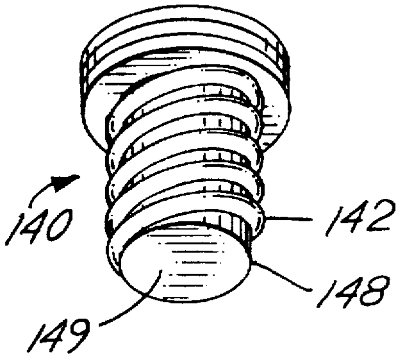
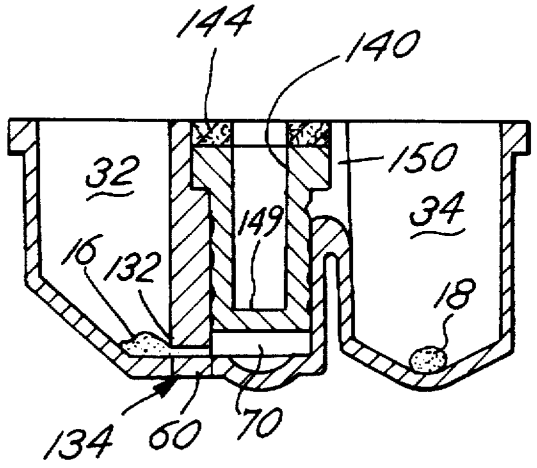
FIG. 22
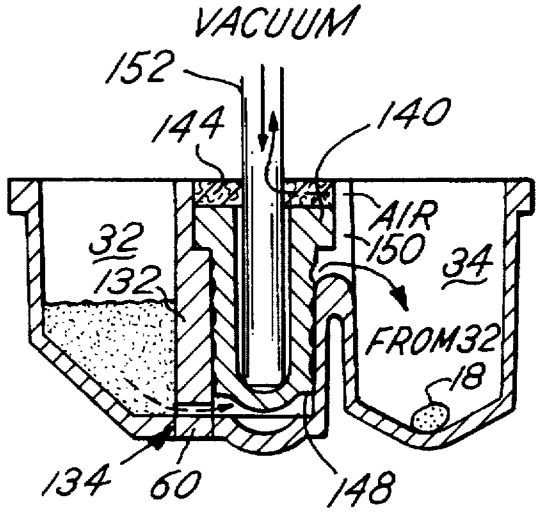
FIG. 23

ADD SAMPLE
HEAT TO 95°C

ADD ENZYME
AMPLIFY AT 42°C

DETECT

VACUUM SYSTEM DIAGRAM

DUAL CHAMBER DISPOSABLE REACTION VESSEL FOR AMPLIFICATION REACTIONS, REACTION PROCESSING STATION THEREFOR, AND METHODS OF USE

BACKGROUND OF THE INVENTION

A. Field of the Invention

This invention relates to the field of the equipment and methods used for performing nucleic acid amplification reactions. More specifically, the invention relates to a novel disposable dual chamber reaction vessel for a nucleic acid amplification reaction and a station for conducting the reaction in the reaction vessel.

B. Description of Related Art

Nucleic acid based amplification reactions are now widely used in research and clinical laboratories for the detection of genetic and infectious diseases. The currently known amplification schemes can be broadly grouped into two classes, based on whether, after an initial denaturing step (typically performed at a temperature of ≧65 degrees C.) for DNA amplifications or for RNA amplifications involving a high amount of initial secondary structure, the reactions are driven via a continuous cycling of the temperature between the denaturation temperature and a primer annealing and amplicon synthesis (or polymerase activity) temperature, or whether the temperature is kept constant throughout the enzymatic amplification process. Typical cycling reactions are the Polymerase and Ligase Chain Reaction (PCR and LCR, respectively). Representative isothermal reaction schemes are NASBA (Nucleic Acid Sequence Based Amplification), Transcription Mediated Amplification (TMA), and Strand Displacement Amplification (SDA). In the isothermal reactions, after the initial denaturation step (if required), the reaction occurs at a constant temperature, typically a lower temperature at which the enzymatic amplification reaction is optimized.

Prior to the discovery of thermostable enzymes, methodologies that used temperature cycling were seriously hampered by the need for dispensing fresh polymerase after each denaturation cycle, since the elevated temperature required for denaturation inactivated the polymerase during each cycle. A considerable simplification of the PCR assay procedure was achieved with the discovery of the thermostable Taq polymerase (from Thermophilus aquaticus). This improvement eliminated the need to open amplification tubes after each amplification cycle to add fresh enzyme. This led to the reduction of both the contamination risk and the enzyme-related costs. The introduction of thermostable enzymes has also allowed the relatively simple automation of the PCR technique. Furthermore, this new enzyme allowed for the implementation of simple disposable devices (such as a single tube) for use with temperature cycling equipment.

TMA requires the combined activities of at least two (2) enzymes for which no optimal thermostable variants have been described. For optimal primer annealing in the TMA reaction, an initial denaturation step (at a temperature of ≧65 degrees C.) is performed to remove secondary structure of the target. The reaction mix is then cooled down to a temperature of 42 degrees C. to allow primer annealing. This temperature is also the optimal reaction temperature for the combined activities of T7 RNA polymerase and Reverse Transcriptase (RT), which includes an endogenous RNase H activity or is alternatively provided by another reagent. The temperature is kept at 42 degrees C. throughout the following isothermal amplification reaction. The denaturation step, which precedes the amplification cycle, however forces the user to add the enzyme after the cool down period in order to avoid inactivation of the enzymes. Therefore, the denaturation step needs to be performed separately from the amplification step.

In accordance with present practice, after adding the test or control sample or both to the amplification reagent mix (typically containing the nucleotides and the primers), the tube is subject to temperatures ≧65 degrees C. and then cooled down to the amplification temperature of 42 degrees C. The enzyme is then added manually to start the amplification reaction. This step typically requires the opening of the amplification tube. The opening of the amplification tube to add the enzyme or the subsequent addition of an enzyme to an open tube is not only inconvenient, it also increases the contamination risk.

The present invention avoids the inconvenience and contamination risk described above by providing a novel dual chamber or "binary" reaction vessel, a reaction processing station therefor, and methods of use that achieve the integration of the denaturation step with the amplification step without the need for a manual enzyme transfer and without exposing the amplification chamber to the environment. The contamination risks from sample to sample contamination within the processing station are avoided since the amplification reaction chamber is sealed and not opened to introduce the patient sample to the enzyme. Contamination from environmental sources is avoided since the amplification reaction chamber remains sealed. The risk of contamination in nucleic acid amplification reactions is especially critical since large amounts of the amplification product are produced. The present invention provides a reaction chamber design that substantially eliminates these risks.

SUMMARY OF THE INVENTION

In a preferred form of the invention, a dual chamber reaction vessel is provided which comprises a single or unit dose of reagents for a reaction requiring differential heat and containment features, such as a nucleic acid amplification reaction (for example, TMA reaction) packaged ready for use. The dual chamber reaction vessel is designed as a single use disposable unit. The reaction vessel is preferably integrally molded into a test strip having a set of wash and reagent wells for use in a amplification product detection station. Alternatively, the reaction vessel can be made as a stand alone unit with flange or other suitable structures for being able to be installed in a designated space provided in such a test strip.

In the dual chamber reaction vessel, two separate reaction chambers are provided in a preferred form of the invention. The two main reagents for the reaction are stored in a spatially separated fashion. One chamber has the heat stable sample/amplification reagent (containing primers, nucleotides, and other necessary salts and buffer components), and the other chamber contains the heat labile enzymatic reagents, e.g., T7 and RT.

The two chambers are linked to each other by a fluid channel extending from the first chamber to the second chamber. A means is provided for controlling or allowing the flow of fluid through the fluid channel from the first chamber to the second chamber. In one embodiment, a membrane is molded into the reaction vessel that seals off the fluid channel. A reciprocable plunger or other suitable structure is provided in the reaction vessel (or in the processing station) in registry with the membrane. Actuation of the plunger causes a breaking of the membrane seal, allowing fluid to flow through the fluid channel. Differential pressure between the two chambers assists in transferring the patient or clinical or control sample through the fluid channel from the first chamber to the second chamber. This can be accomplished by applying pressure to the first chamber or applying vacuum to the second chamber.

Other types of fluid flow control means are contemplated, such as providing a valve in the fluid channel. Several different valve embodiments are described.

In use, the fluid sample is introduced into the first chamber and the first chamber is heated to a denaturation temperature (e.g., 95 degrees C.). After the amplification reagents in the first chamber have reacted with the fluid sample and the denaturation process has been completed, the first chamber is quickly cooled to 42 degrees C. for primer annealing. The two chambers of the reaction vessel are not in fluid communication with each other prior to completion of the denaturation and cooling step. After these steps are complete, the means for controlling the flow of fluid is operated to allow the reaction solution to pass through the fluid channel from the first chamber to the second chamber. For example, the valve in the fluid channel is opened and the fluid sample is directed into the second chamber either by pressure or vacuum techniques. The reaction solution is then brought into contact with the amplification enzyme(s) (e.g., T7 and/or RT) and the enzymatic amplification process proceeds in the second chamber at 42 degrees C.

In a preferred embodiment, after completion of the reaction, a SPR® (solid phase receptacle) pipette-like device is introduced into the second chamber. Hybridization, washing and optical analysis then proceeds in accordance with well known techniques in order to detect the amplification products.

An integrated stand-alone processing station for processing a reaction in the dual chamber reaction vessel in accordance with presently preferred embodiments of the invention is described. The processing station includes a tray for carrying in proper alignment a plurality of test strips, a temperature control subassembly for maintaining the two chambers of the reaction vessel at the proper temperatures, a mechanism to open the fluid channel connecting the two chambers together, and a vacuum subassembly for providing vacuum to the second chamber to draw the fluid sample from the first chamber into the second chamber.

BRIEF DESCRIPTION OF THE DRAWINGS

Presently preferred embodiments of the invention will be described in conjunction with the appended drawings, wherein like reference numerals refer to like elements in the various views, and in which:

FIG. 10 is a top plan view of the dual chamber reaction vessel of FIGS. 5–9 shown enlarged;

FIG. 11 is a detailed cross section of the dual chamber reaction vessel with the lower cap removed as in FIG. 9, and with the plunger removed;

FIG. 12 is a detailed cross section of the dual chamber reaction vessel with the lower cap and plunger installed as they would be in use;

FIG. 13 is a perspective view of the plunger of FIG. 12;

FIG. 14 is another perspective view of the plunger;

FIG. 15 is an elevational view of the plunger;

FIG. 21 is perspective view of an alternative construction of the stand-alone disposable dual chamber reaction vessel of FIG. 19;

FIG. 22 is a cross-sectional view of the embodiment of FIG. 21;

FIG. 23 is a cross-sectional view of the embodiment of FIG. 21 showing the action of the helical thimble valve being deformed by a vacuum plunger and the flow of fluid sample from the first chamber into the second chamber;

FIG. 24 is a perspective view of the helical thimble valve of FIGS. 22 and 23;

DETAILED DESCRIPTION OF THE PREFERRED AND ALTERNATIVE EMBODIMENTS OF THE INVENTION

Overview

A preferred form of the invention provides for a dual chamber or "binary" reaction vessel. The term "binary" refers to the characteristic of the vessel of storing in a spatially separated fashion at least two different reagents, for example a heat stable sample/amplification reagent(s) containing, for example, primers and nucleotides in one chamber and heat labile enzyme(s) such as T7 and RT in the second chamber. The reagents within the two chambers are not in contact prior to completion of the denaturation and cooling steps. The first chamber is accessible via a pierceable membrane or other means so as to permit a patient or clinical or control sample(s) in liquid form to be added into the first chamber. The second chamber is sealed and contains the enzymatic components of the amplification reaction. The enzymatic components may be in several physical forms, such as liquid, pelletized, lyophilized, etc. After the contents of the first chamber is brought into contact with the second chamber, the reaction can then take place, such as in the second chamber.

In one possible form of the invention, the two chambers may be part of an integrated disposable unit. In another possible embodiment, the two chambers may be two distinct units which have complementary engaging surfaces or features that allow the two units to be combined into a single unit. In the first embodiment, where the two chambers are part of a unitary article, the unit must be made to prohibit the exchange of materials between the two chambers during shipping and prior to the denaturation (heating) step. In both embodiments, a mechanism is required by which the contents of the first chamber (the patient or test sample and amplification reagent(s) mix after denaturation and primer annealing) is brought into contact with the enzyme(s) in the second chamber. The mechanism operates to introduce the contents of the first chamber into the second chamber following the completion of the denaturation step and the cooling of the patient sample/amplification mix to the appropriate temperature for the enzymatic amplification reaction, e.g., 42 degrees C. Several different mechanisms are described in detail herein.

Figure 1:
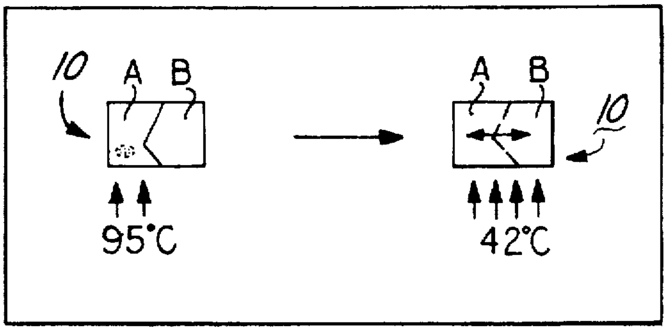
FIG. 1 is a schematic representation of a disposable dual chamber reaction vessel and the heating steps associated therewith to perform an isothermal amplification reaction, i.e., a TMA reaction, in accordance with one possible embodiment of the invention.

FIG. 1 is a schematic representation of a disposable dual chamber reaction vessel 10 and the heating steps associated therewith to perform an isothermal reaction, i.e., a TMA reaction, in accordance with one possible embodiment of the invention. Chamber A contains the amplification reagents or mix, namely deoxynucleotides, primers, $MgCl_2$ and other salts and buffer components. Chamber B contains the amplification enzyme(s) that catalyzes the amplification reaction, e.g., T7 and/or RT. After addition of the targets (or patient sample) into chamber A, heat is applied to chamber A to denature the DNA nucleic acid targets and/or remove RNA secondary structure. The temperature of chamber A is then quickly cooled down to allow primer annealing. Subsequently, the solution of chamber A is brought into contact with chamber B. Chambers A and B, now in fluid communication with each other, are then maintained at the optimum temperature for the amplification reaction, e.g., 42 degrees C. By spatially separating chamber A from chamber B, and applying the heat for denaturation to chamber A only, the thermolabile enzymes in chamber B are protected from inactivation during the denaturation step.

Figure 2:
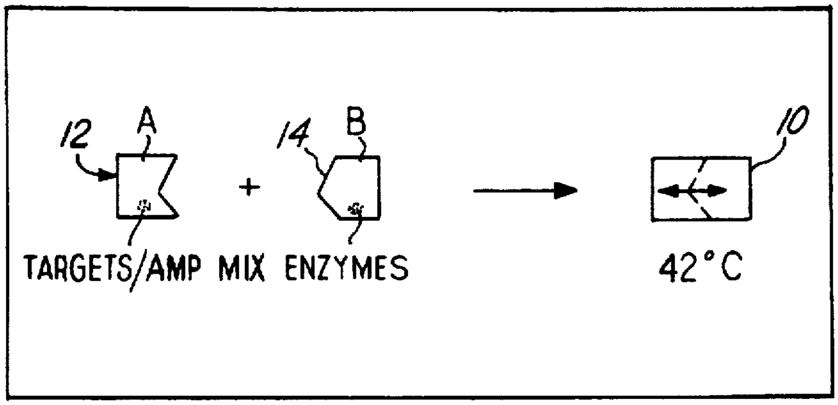
FIG. 2 is a schematic representation of alternative form of the invention in which two separate reaction chambers are combined to form a dual chamber reaction vessel.

FIG. 2 is a schematic representation of an alternative form of the invention in which two separate reaction chambers 12 and 14 are combined to form a dual chamber reaction vessel 10. Like the embodiment of FIG. 1, Chamber A is pre-loaded during a manufacturing step with an amplification reagent(s) or mix, namely nucleotides, primers, $MgCl_2$ and other salts and buffer components. Chamber B is pre-loaded during manufacturing with the amplification enzyme(s) that catalyzes the amplification reaction, e.g., T7 and/or RT. Fluid sample is then introduced into chamber A. The sample is heated for denaturation of nucleic acids to 95 degrees C. in chamber A. After cooling chamber A to 42 degrees C., the solution in chamber A is brought into contact with the enzymes in chamber B to trigger the isothermal amplification reaction.

If the reaction vessel is designed such that, after having brought the contents of chambers A and B into contact, the amplification chamber does not allow any exchange of materials with the environment, a closed system amplification is realized which minimizes the risk of contaminating the amplification reaction with heterologous targets or amplification products from previous reactions or the environment.

Figure 3:
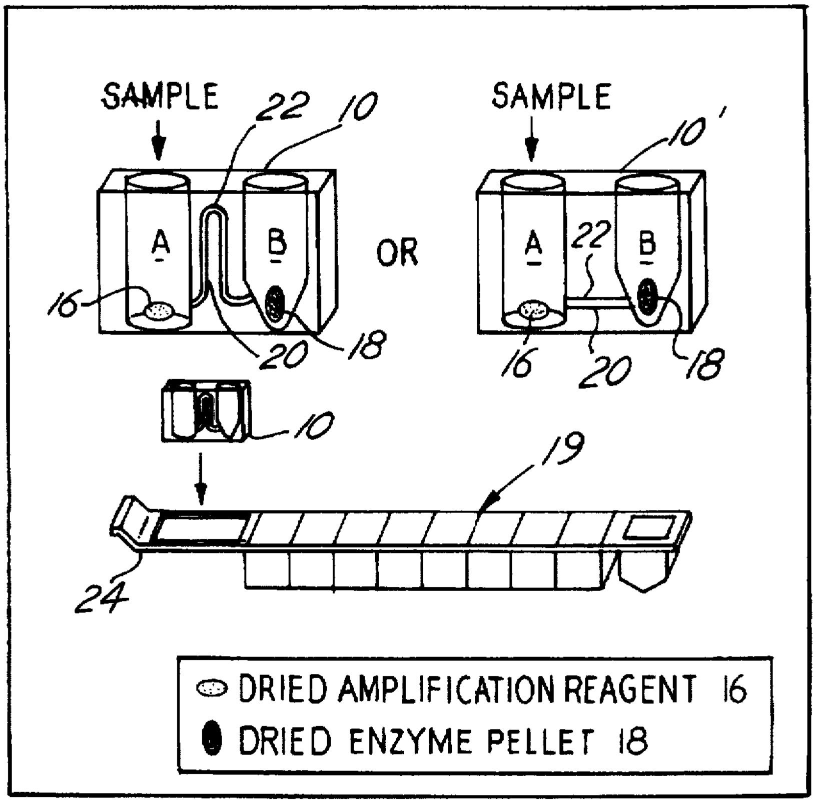
FIG. 3 is a schematic representation of two alternative embodiments of a dual chamber reaction vessel that are snapped into place in a test strip for processing with a solid phase receptacle and optical equipment in accordance with a preferred embodiment of the invention.

FIG. 3 is a schematic representation of two alternative dual chamber reaction vessels 10 and 10' that are snapped into place in a test strip 19 for processing with a solid phase receptacle and optical equipment in accordance with a preferred embodiment of the invention. In the embodiments of FIG. 3, a unidirectional flow system is provided. The sample is first introduced into chamber A for heating to the denaturation temperature. Chamber A contains the dried amplification reagent mix 16. After cooling, the fluid is transferred to chamber B containing the dried enzyme(s) 18 in the form of a pellet. Chamber B is maintained at 42 degrees C. after the fluid sample is introduced into Chamber B. The amplification reaction takes place in Chamber B at the optimum reaction temperature (e.g., 42 degrees C.). After the reaction is completed, the test strip 19 is then processed in a machine such as the VIDAS instrument commercially available from bioMérieux Vitek, Inc., Hazelwood, Mo., the assignee of the present invention. Persons of skill in the art are familiar with the VIDAS instrument.

The unidirectional flow features could be provided by a suitable one-way valve such as check valve 20 in the fluid conduit 22 connecting chambers A and B. The action of transferring the fluid from chamber A to chamber B could be by any of several possible methods, such as by introduction of fluid pressure in the solution in chamber A (such as by a piston), or applying a vacuum to chamber B to draw the solution through the fluid channel 22. Examples of these methods are described in detail below.

The steps of heating and cooling of chamber A could be performed prior to the insertion of the dual chamber disposable reaction vessel 10 or 10' into the test strip 16, or, alternatively, suitable heating elements could be placed adjacent to the left hand end 24 of the test strip 19 in order to provide the proper temperature control of the reaction chamber A. The stand alone amplification processing station of FIGS. 31–40, described below, incorporates suitable heating elements and control systems to provide the proper temperature control for the reaction vessel 10.

Figure 4:
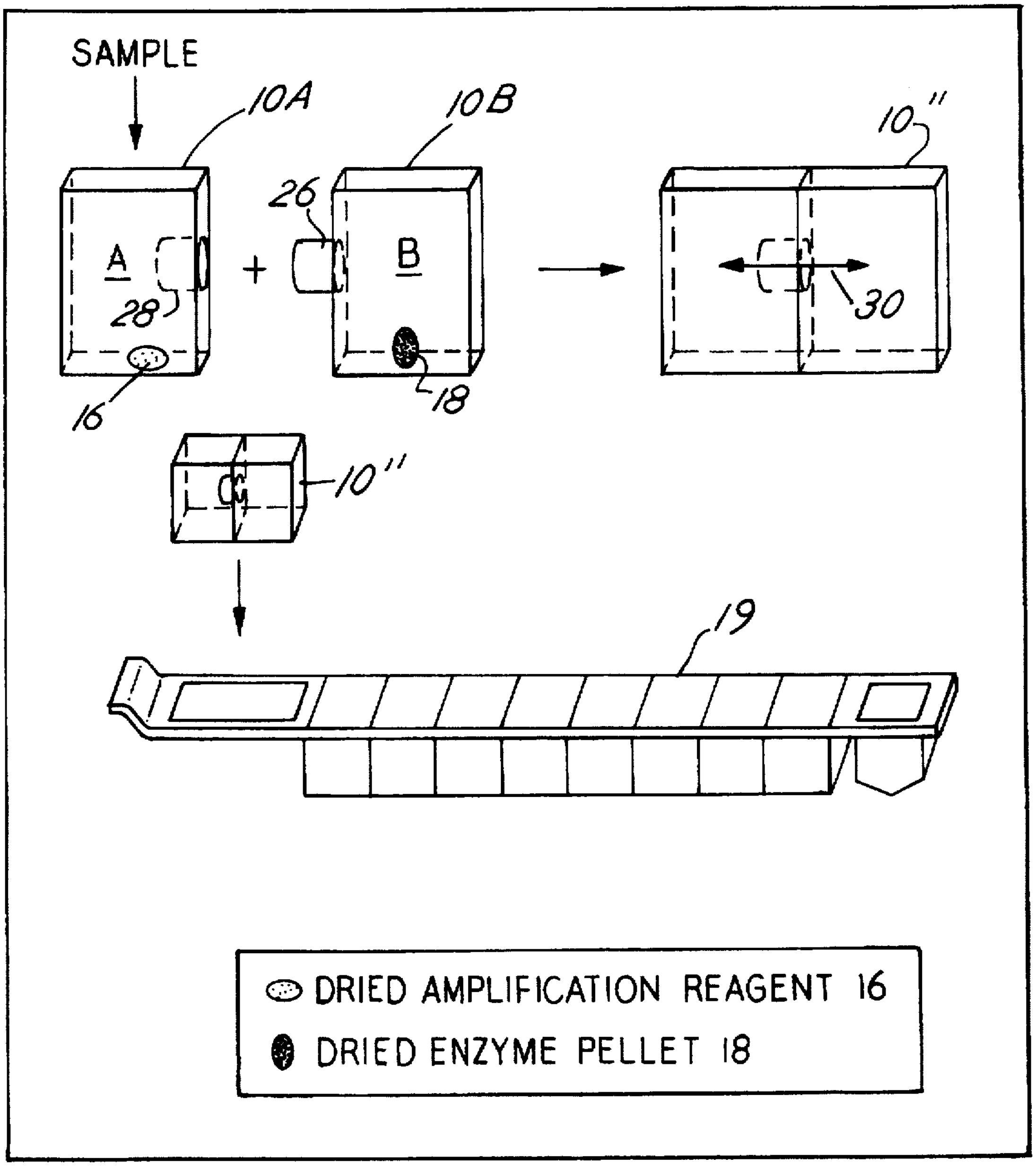
FIG. 4 is a schematic representation of an alternative embodiment of a dual chamber reaction vessel formed from two separate chambers that are combined in a manner to permit a fluid sample in one chamber to be transferred to the other chamber, with the combined dual chamber vessel placed into a test strip such as illustrated in FIG. 3.

FIG. 4 is a schematic representation of an alternative embodiment of a dual chamber reaction vessel 10" formed from two separate interlocking vessels 10A and 10B that are combined in a manner to permit a fluid sample in one chamber to flow to the other, with the combined dual chamber vessel 10" placed into a test strip 19 such as described above in FIG. 3. The fluid sample is introduced into chamber A, which contains the dried amplification reagent mix 16. Vessel A is then heated off-line to 95 degrees C., then cooled to 42 degrees C. The two vessels A and B are brought together by means of a conventional snap fit between complementary locking surfaces on the tube projection 26 on chamber B and the recessed conduit 28 on chamber A. The mixing of the sample solution from chamber A with the enzyme(s) from chamber B occurs since the two chambers are in fluid communication with each other, as indicated by the arrow 30. The sample can then be amplified in the combined dual chamber disposable reaction vessel 10" off-line, or on-line by snapping the combined disposable vessel 10" into a modified VIDAS strip. The VIDAS instrument could perform the detection of the amplification reaction products in known fashion.

Dual Chamber Reaction Vessel Embodiment With Pierceable Membrane

Figure 5:
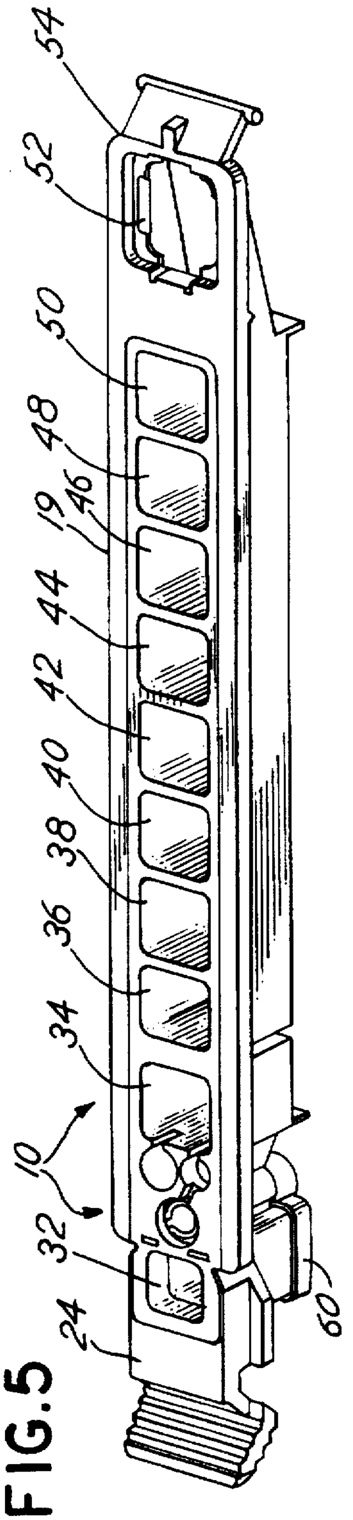
FIG. 5 is a detailed perspective view of a disposable test strip in which one embodiment of the dual chamber reaction vessel is integrally molded into the test strip at the left-hand end of the test strip.

FIG. 5 is a detailed perspective view of a modified disposable test strip 19 similar to that used in the VIDAS instrument in which a dual chamber reaction vessel 10 comprising a first chamber 32 and a second chamber 34 is integrally molded into the test strip 19 at the left-hand end 24 of the test strip. The test strip 19 includes a plurality of wells to the right of the dual chamber reaction vessel 10.

These wells include a probe well 36, a hybridization well 38, an empty well 40, four wash buffer wells 42, 44, 46 and 48, and a well 50 for containing a bleach solution. A substrate cuvette 52 is inserted into the opening 52 at the right hand end 54 of the strip for performance of optical analysis. The test strip 19 is used in conjunction with a SPR®, not shown in the drawings, which is used to draw a fluid sample out of the amplification well 34. The SPR is then dipped into the other wells 36–50 during the test procedure in known fashion to perform the analysis, for example as performed in the commercially available VIDAS instrument.

Figure 6:
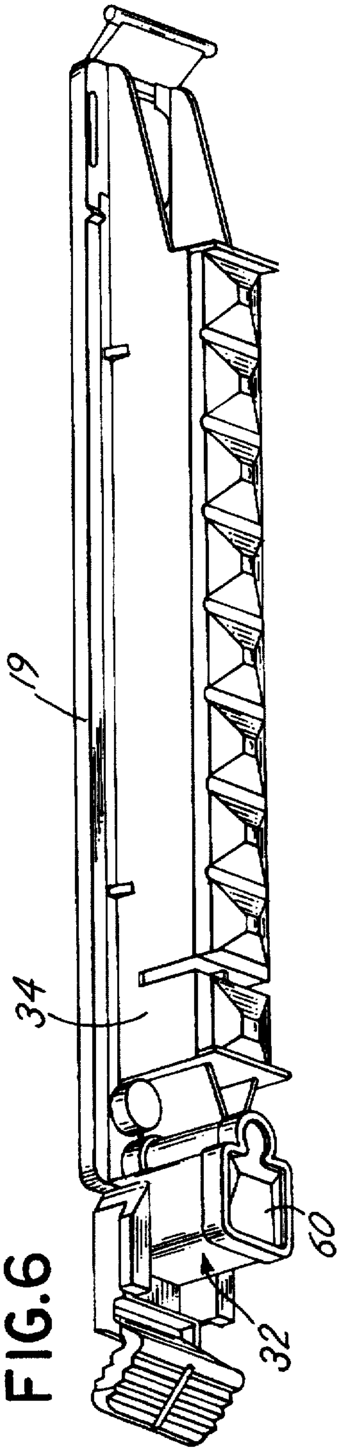
FIG. 6 is detailed perspective view of the disposable test strip of FIG. 5 as seen from below.
Figure 7:
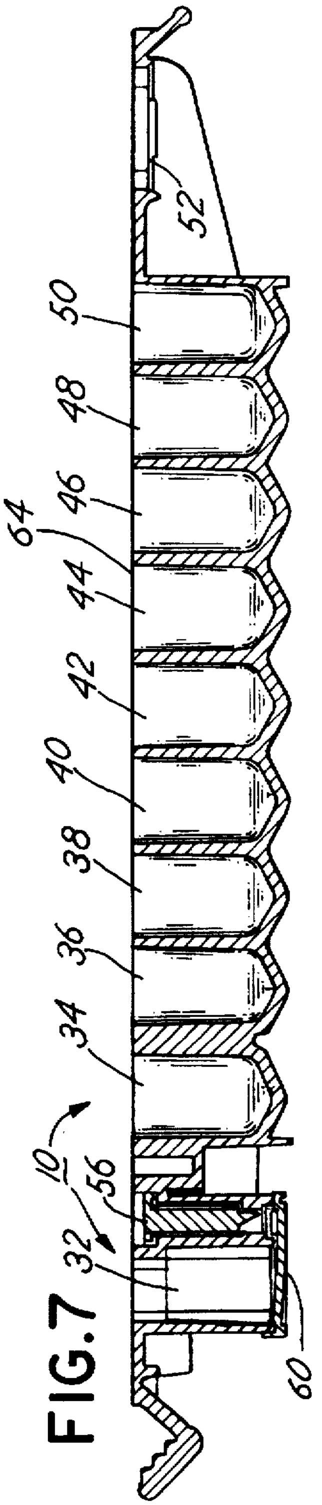
FIG. 7 is a cross section of the disposable test strip of FIGS. 5 and 6, showing a plunger having a chisel-like tip that is used to pierce a membrane in a fluid channel connecting the two chambers together to thereby allow the fluid to pass from the first chamber into the second chamber.

FIG. 6 is a detailed perspective view of a disposable test strip of FIG. 5 as seen from below. FIG. 7 is a cross section of the disposable test strip of FIGS. 5 and 6, showing a plunger 56 having a chisel-like tip at the lower end thereof that is used to pierce a membrane in a fluid channel connecting the two chambers 32 and 34 together to thereby allow the fluid to pass from the first chamber 32 into the second or amplification chamber 34.

Figure 8:
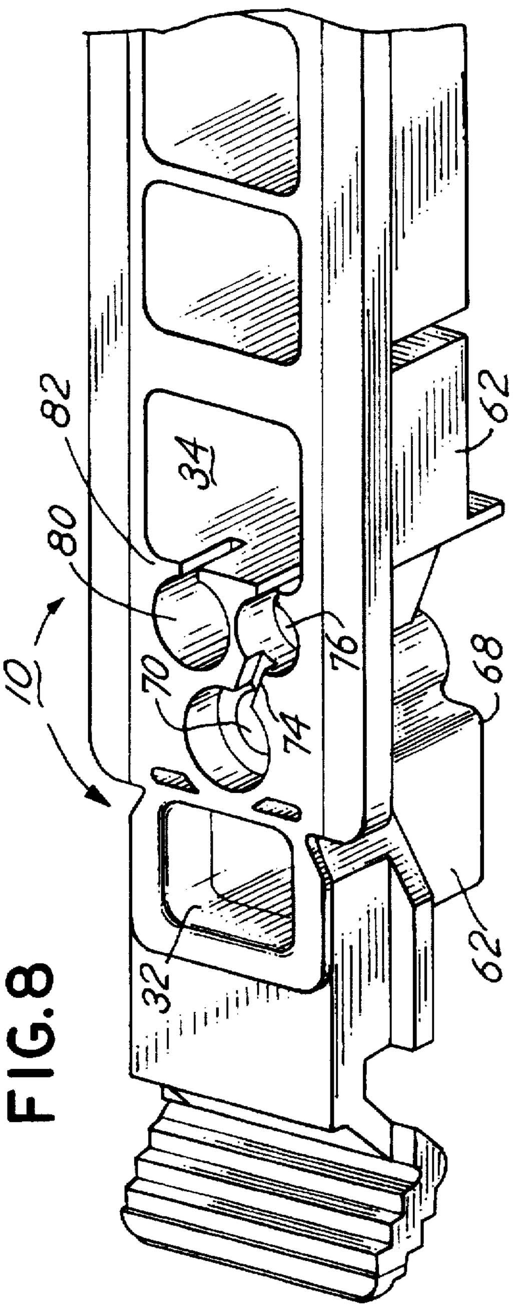
FIG. 8 is a perspective view of the left hand end of the test strip of FIGS. 5–7 shown enlarged in order to better illustrate the dual chamber reaction vessel.
Figure 9:
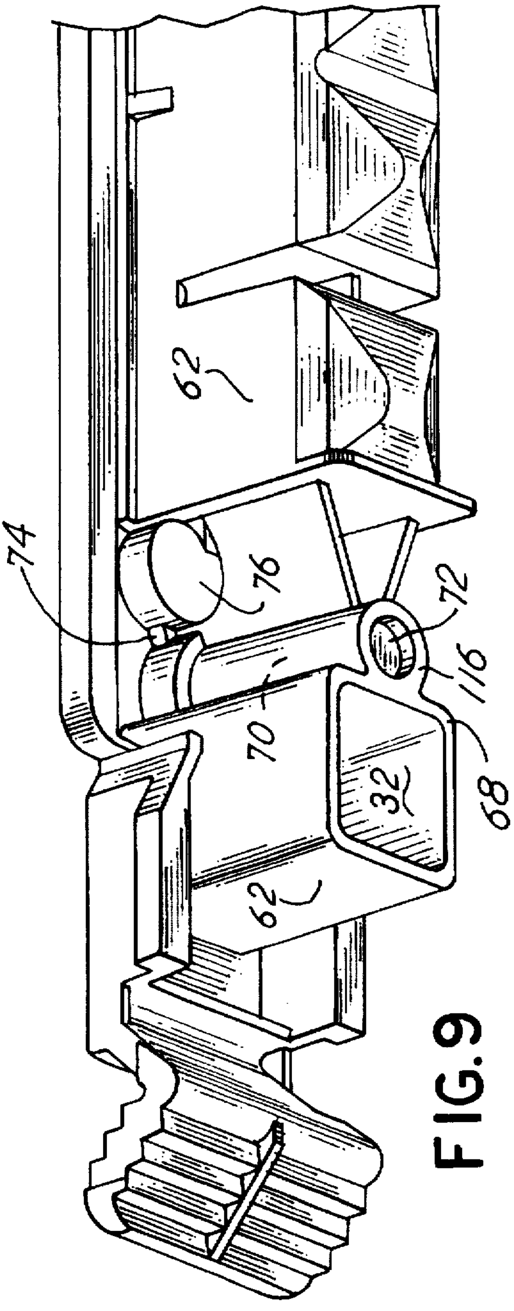
FIG. 9 is a detailed perspective view of a disposable test strip of FIG. 5 as seen from below shown greatly enlarged, and with the cap covering the base of the first chamber and intermediate chamber removed.

FIG. 8 is a perspective view of the left hand end of the test strip of FIGS. 5–7 shown enlarged in order to better illustrate the dual chamber reaction vessel 10. FIG. 9 is a detailed perspective view of a disposable test strip of FIG. 5 as seen from below shown greatly enlarged, and with a cap 60 (FIG. 12) covering the base of the first chamber and the intermediate chamber or fluid channel removed to better illustrate the structure of the device.

FIG. 10 is a top plan view of the dual chamber reaction vessel of FIGS. 5–9 shown enlarged. FIG. 11 is a detailed cross section of the dual chamber reaction vessel with the lower cap removed as in FIG. 9, and with the plunger removed. FIG. 12 is a detailed cross section of the dual chamber reaction vessel with the lower cap 60 and plunger 56 installed as they would be in use.

Referring to FIGS. 5–12, the test strip 19 includes a molded body 62 that defines the walls of a reaction vessel 10. The vessel 10 includes a first chamber 32 in which a dried amplification reagent mix is placed at the bottom of the chamber 32 during manufacturing of the test strip 19. Polypropylene is a suitable material for use in molding the device 10 and test strip 19, and a thickness of 40 mils for the walls defining the chambers 32 and 34 is adequate in the illustrated operational embodiment. The wells of the test strip, including the first and second chambers 32 and 34, respectively, are covered with a thin film or membrane 64 after manufacture, shown in FIGS. 7, 11, 12, to seal all of the wells and reaction vessel 10. The membrane (such as PET, commonly known as MYLAR, or aluminum foil with a moreprine polyethylene/polypropylene mix adhesive) is removed from FIGS. 5, 8 and 10 in order to illustrate the structures in the test strip 19.

The bottom of the first chamber 32 is capped by a cap 60 that is ultrasonically welded to the bottom surface 68 of the walls defining the first chamber. The cap 60 is shown greatly enlarged in FIGS. 16–18 and discussed below. The cap 60 provides a fluid passage from the base of the first chamber 32 to the base of an intermediary fluid passage 70 connecting the first chamber 32 to the second chamber 34. A plunger 56 with a chisel-like tip is positioned in the intermediary fluid passage 70. The chisel tip of the plunger 56 breaks a membrane or seal 72 (FIG. 9) in the fluid passage (flashed molded in the fluid passage during molding) when the plunger 56 is depressed from above. This allows fluid to migrate from the first chamber 32 into the fluid passage 70, up along the side of the plunger 56 and into a second channel 74 (FIGS. 8 and 10) communicating with a enzyme pellet chamber 76 that contains the enzyme pellet (not shown). The fluid sample dissolves the enzyme pellet as it travels through the enzyme pellet chamber 76 into the second or amplification chamber 34 (see FIG. 8).

A vacuum port 80 (FIG. 8) is provided in fluid communication with the second chamber 34. A Porex polyethylene filter (not shown) is positioned within the vacuum port 80. Vacuum is used to effectuate the transfer of the fluid sample from the first chamber 32 to the second chamber 34 after the plunger 56 has been moved to the lower position to break the seal 72. A vacuum implement containing a vacuum probe or tube (see e.g., FIG. 33) is inserted into the vacuum port 80 in a manner such that a seal is formed in the top surface 82 of the strip adjacent the vacuum port 80. Vacuum is drawn in the vacuum tube. The pressure difference resulting from ambient pressure in the first chamber 32 and a vacuum in the second chamber 34 draws fluid up the intermediate chamber or fluid passage 70 and into the channel 74 and pellet chamber 76 and into the second chamber 34.

FIG. 13 is an isolated perspective view of the plunger 56 of FIG. 12. FIG. 14 is another perspective view of the plunger 56, shown from below. FIG. 15 is an elevational view of the plunger 15. Referring to FIGS. 13–15, the plunger includes a cylindrically-shaped body 90 having a chisel 92 at the lower end thereof and a head portion 94. The head portion 94 includes a circular ring 96 with voids 98 formed therein to promote the drawing of a vacuum in the intermediate chamber 70 (FIGS. 8–12) in which the plunger is installed. The head 94 has downwardly depending feet 100 that seat on a rim 102 (FIG. 11) inside the intermediate chamber 70 when the plunger 65 has been depressed to its lowermost position, as shown in FIG. 12. The chisel 92 has a tip 104 that breaks through the seal or membrane 72 obstructing the passage of fluid up the intermediate channel 70. The seal 72 is best showing FIGS. 9, 11 and 12. FIG. 12 shows the placement of the chisel 92 just above the seal 72 as it would be while the heating to 95 degrees C. in the first chamber 32 is occurring and during the cool-down period.

As shown in FIG. 14, the plunger has a V-shaped groove 106 in the side of the plunger body 90 that provides a channel for fluid to rise up the length of the cylindrical body 90 of the plunger to the elevation of channel 74 (FIG. 10) connecting the intermediate chamber 70 with the enzyme pellet chamber 76.

Figure 16:
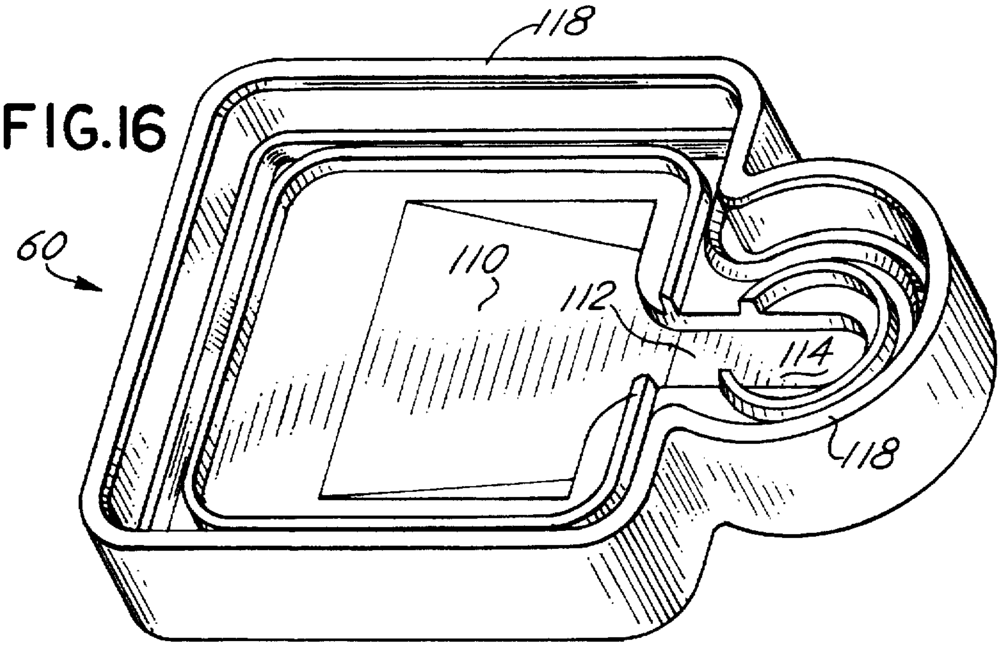
FIG. 16 is a perspective view of the cap that covers the base of the first chamber and the intermediate chamber of the reaction vessel of FIGS. 8 and 9.
Figure 17:
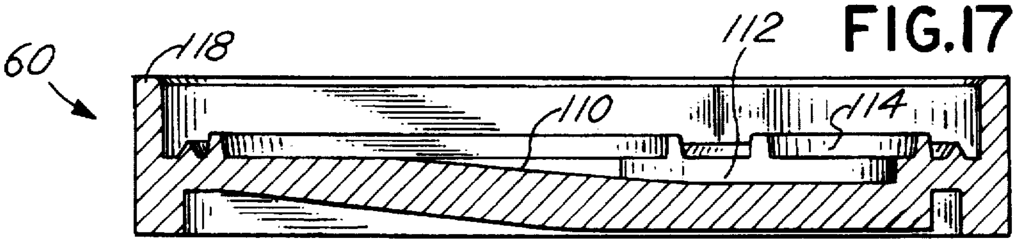
FIG. 17 is a cross-section of the cap of FIG. 16.
Figure 18:
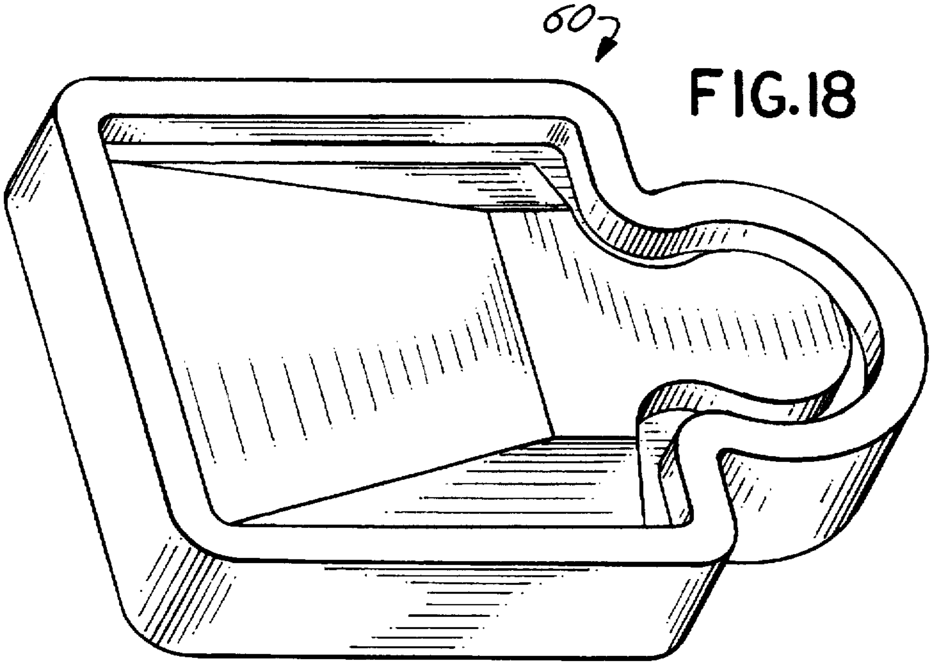
FIG. 18 is a perspective view of the base of cap of FIG. 16.

FIG. 16 is a perspective view of the top surface of the cap 60 that covers the base of the first chamber of the reaction vessel of FIGS. 8 and 9, shown greatly enlarged. FIG. 17 is a cross-section of the cap 60 of FIG. 16. FIG. 18 is a perspective view of the base of cap 60. Referring to these figures, in conjunction with FIGS. 6 and 9, it will be seen from FIG. 8 that without the cap 60 there is no base to the first chamber 32 and no fluid passage between the first chamber 32 and the intermediary chamber 70. The cap 60 provides the base of the first chamber 32 and the passage between the first chamber 32 and the intermediate chamber 70. The cap 60 includes a shallow tray 110 positioned to form a base of the first chamber 32. The tray 110 slopes downwardly to a small passage 112 linking the shallow tray 110 to a circularly shaped reservoir 114 that is in vertical alignment with the circular wall 116 of the intermediate chamber (see FIG. 9). The semirectangular and semicircular rim 118 of the cap 60 is ultrasonically bonded to the bottom portions 68 and 116 of the first and intermediate chambers, respectively, as shown in FIG. 6. In the installed condition, when the fluid sample has been introduced into the first chamber 32, the fluid will pass into the channel 112 and reservoir 114, immediately below the seal 72 in the intermediate chamber (see FIG. 9). Thus, when the seal 72 is broken by the plunger 56 and vacuum is drawn from the vacuum port 80 of FIG. 8, the solution of the fluid sample and reagent from the first chamber 32 will be drawn up the side of the plunger 56 and into the enzyme pellet chamber 76, dissolving the pellet, and into second chamber 34 where the amplification reaction takes place.

Referring to FIG. 5, after the amplification reaction has occurred in the second chamber 34 at the proper temperature, the SPR (not shown) is lowered into the second chamber 34 and a portion of the amplified sample is withdrawn into the SPR. The SPR and test strip are moved relative to each other such that the SPR is positioned above the adjacent probe well 36, whereupon it is lowered into the probe well 36. The rest of the analytical processes with the SPR and test strip are conventional and well known in the art. For example, the process may be implemented in the manner performed by the VIDAS instrument of the applicants' assignee.

Figure 19:
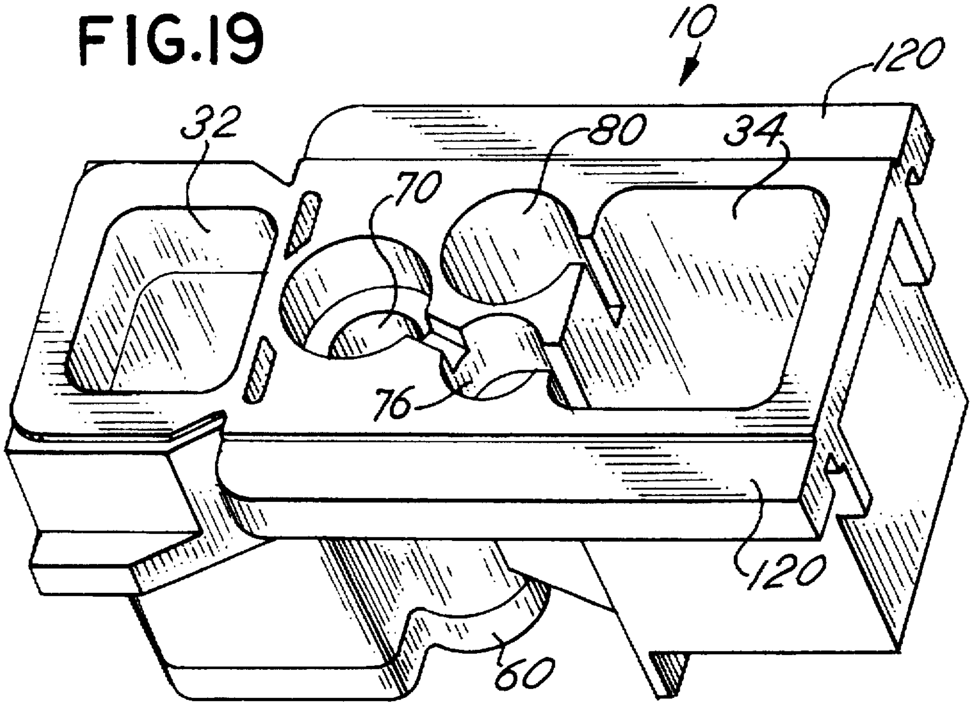
FIG. 19 is a perspective view of a stand-alone disposable dual chamber reaction vessel that is designed to snap into the test strip of the type shown in FIG. 5 in the manner suggested in FIG. 4.
Figure 20:
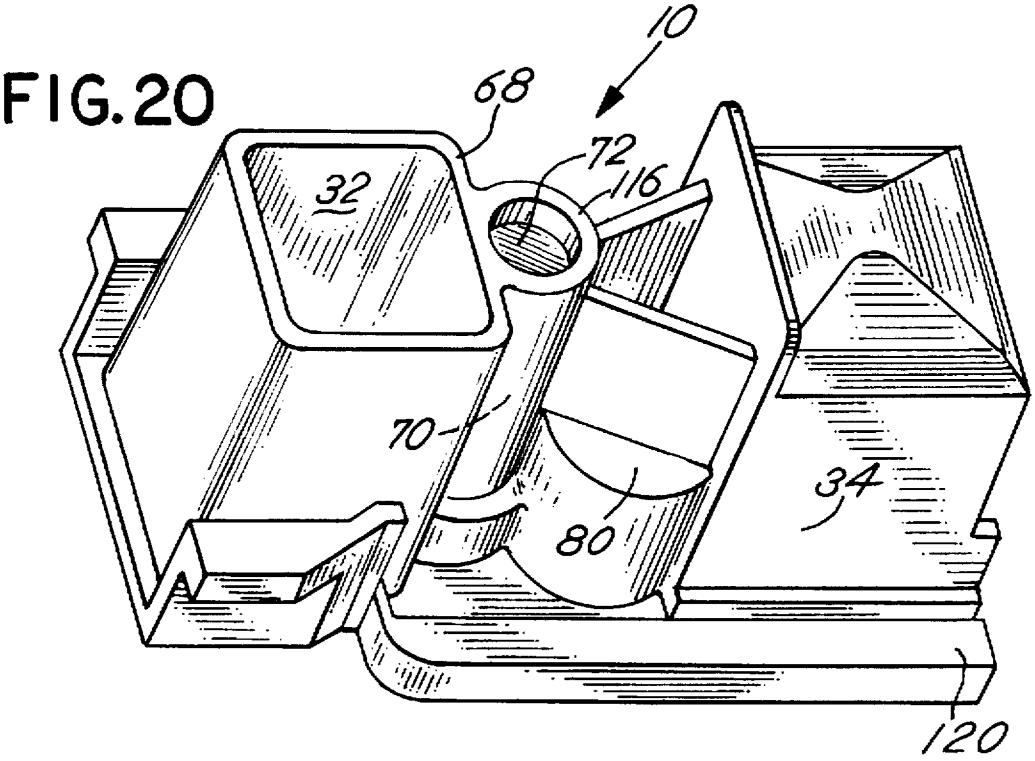
FIG. 20 is a perspective view of the stand-alone disposable dual chamber reaction vessel of FIG. 19, with a lower cap as shown in FIGS. 16–18 removed.

FIG. 19 is a perspective view of a stand-alone disposable dual chamber reaction vessel 10 that is designed to snap into the test strip 19 of the type shown in FIG. 5 in the manner suggested in FIG. 4. FIG. 20 is a perspective view of the stand-alone disposable dual chamber reaction vessel of FIG. 19 shown upside down, with a lower cap constructed as shown in FIG. 16–18 to cover the base of the first chamber 32 and intermediate chamber 70 removed. A thin film or foil type membrane is applied to the top surface of the reaction vessel 10, in a manner to cover the first chamber 32, the intermediate chamber 34, enzyme pellet chamber 76, second chamber 34 and vacuum port 80. The film is not shown in FIG. 19 in order to better illustrate the structures of the reaction vessel 10. Further, a plunger for the intermediate chamber 70 is also not shown. Once the stand-alone disposable reaction vessel of FIGS. 19 and 20 has been installed into the test strip, the operation of the embodiment of FIGS. 19 and 20 is exactly as described above.

To accommodate the vessel of FIGS. 19 and 20 into the test strip 19 of FIGS. 5 and 6, the test strip 19 is modified by providing an aperture in the left hand end 24 of the test strip adjacent to the probe well 36, and providing suitable rail structures to allow a pair of flanges 120 on the periphery of the unit 10 to snap into the test strip 19. Of course, it will be understood that after molding of the reaction vessel of FIG. 19, the nucleic acid and amplification reagent will be added to the first chamber 32, and the enzyme pellet is added to the enzyme pellet chamber 76. Then, the film covering the entire top surface of the vessel 10 will be applied to seal the chambers. The device is then ready for use as described herein.

Dual Chamber Reaction Vessel Embodiment With Elastomeric Thimble Valve

Figure 25:
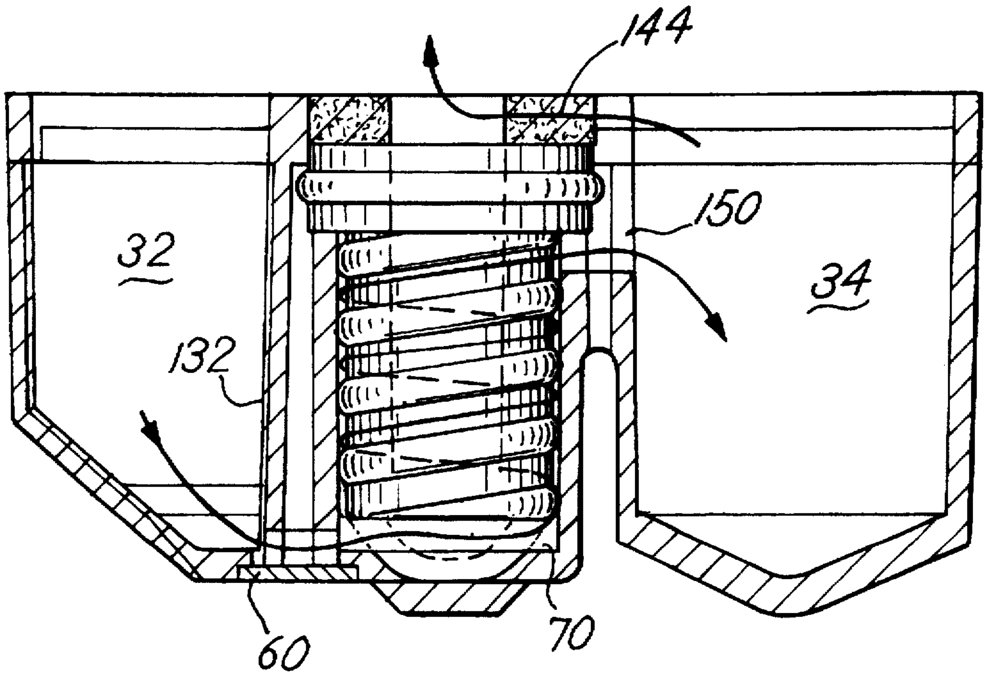
FIG. 25 is a sectional view of the embodiment of FIG. 21 showing the flow of fluid through the device from the first chamber into the second chamber.

FIG. 21 is perspective view of yet another alternative construction of the disposable dual chamber reaction vessel 10 of FIG. 19 that can be molded into the test strip or made as a separate unit to snap into a test strip 19 as described above. The vessel 10 has a first chamber 32 and a second chamber 34 and an intermediate chamber 70 linking the two chambers 32 and 34 together. The base of the first chamber 32 has a hole that is plugged with a cap 60 that is ultrasonically welded to the base of the housing 130. The cap 60 is spaced slightly from the bottom surface of a wall 132 forming the side of the first chamber 32, thereby defining a small passage 134 for fluid to flow out of the first chamber into the intermediate chamber 70. Amplification reagents 16 for the denaturation step are loaded into the base of the chamber 32 of the reaction vessel 10, as shown in FIG. 25. An enzyme pellet 18 is loaded into the secondary chamber 34.

An elastomeric thimble-shaped valve element 140 having helical rib features 142, shown isolated in FIG. 24, is positioned in the intermediate chamber 70. FIG. 22 is a cross-sectional view of the embodiment of FIG. 21, showing the thimble valve 140 in the intermediate chamber 70. A filter 144 is positioned above the top of the thimble valve 144. In its relaxed state, a lower circumferential rib 148 on the thimble valve 140 and the exterior surfaces of the helical rib feature 142 on the side walls of the thimble valve 140 make contact with the wall of the intermediate chamber 70, sealing off the chamber 70 and preventing fluid from passing from the gap 134 separating the cap 60 from the wall 132, up the intermediate chamber 70 and into the secondary chamber 34.

The resilient thimble valve 140 is deformable such that the lower circumferential rib 148 may be moved away from the wall of the intermediate chamber 70. This is achieved by inserting an element 152 into the interior of the thimble valve 140 and pressing on the wall portion 149 of the valve 140 to stretch and deform the end wall and adjacent shoulder of the thimble valve. FIG. 23 is a cross-sectional view of the embodiment of FIG. 21 showing the action of the helical thimble valve 140 being deformed by a vacuum plunger 152 that is inserted into the interior of the thimble valve 140. The end of the vacuum plunger presses against the wall 149, as shown in FIG. 23, pulling the lower circumferential rib away from the wall of the intermediate chamber 70. The helical rib feature 142 stays in contact with the cylindrical wall of the chamber 70. At the same time, vacuum is drawn through an aperture in the side of the vacuum plunger 152 to pull air out of the secondary chamber 34 and through the filter 144 into the vacuum plunger 152. This vacuum action draws fluid out of the base of the first chamber 32, and up vertically in a helical path along the helical port defined between the helical rib feature 142 and the wall of the intermediate chamber 70. Substantially all of the patient sample/reagent solution in the first well 32 is removed in accordance with this embodiment. The solution passes from the upper end of the helical feature 142 into a gap 150 connecting the intermediate chamber 70 with the second chamber 34. This is illustrated best in FIGS. 23 and 25.

The embodiment of FIGS. 21–23 has the advantage that the opening of the thimble valve 140 tends to cause any oil in the amplification reagent mix in the first chamber that may find its way to the base of the intermediate chamber 70 to be blown back toward the first chamber, acting in the manner of a common plunger, and allow the fluid sample and reagent solution to take its place. Where the amplification reagent contains an oil such as a silicone oil, it is important that the oil is not the first substance to migrate into the second chamber, as this can cause the oil to coat the enzyme pellet in the second chamber, which can interfere with the amplification reaction in the second chamber 34. Thus, preferably the thimble valve 140 is designed such that when the wall 149 of the thimble valve 140 is activated by the vacuum probe 152, any oil that may lie at the base of the intermediate chamber 70 is initially forced back into the first chamber 32. Once the lower rib 148 of the thimble valve 140 is moved away from the wall of the intermediate chamber 70, the drawing of the vacuum in the second chamber allows the fluid sample/reagent solution to be drawn into the second chamber as described above.

Test Strip With Enzyme Carrier Embodiment

Figure 27:
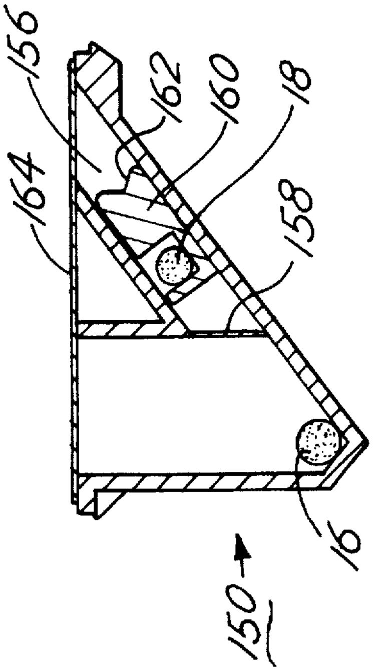
FIG. 27 is a cross-section of the embodiment of FIG. 26, showing an enzyme plunger carrying an enzyme pellet for introduction into the amplification well.
Figure 26:
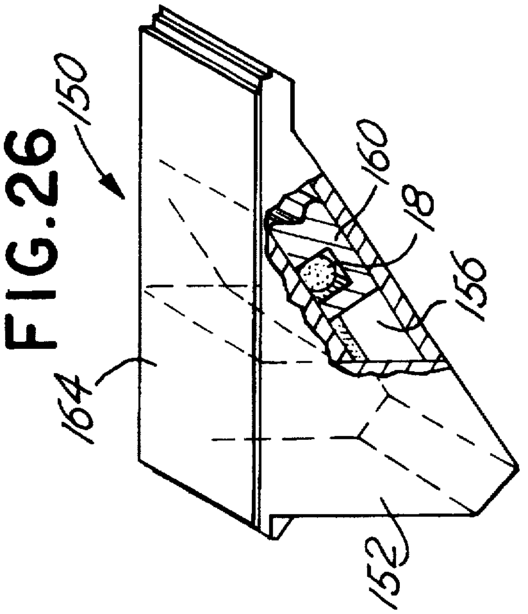
FIG. 26 is a perspective view of another embodiment of the disposable reaction chamber in accordance with the invention designed to snap into the test strip in the manner suggested in FIG. 4.

FIG. 26 is a perspective view of yet another embodiment of the disposable reaction vessel 150 in accordance with the invention. The reaction vessel 150 is designed to snap into the test strip 19 of FIG. 8 in the manner suggested in FIG. 4 and described above. FIG. 27 is a cross-section of the embodiment of FIG. 26. Referring to FIGS. 26 and 27, the disposable reaction vessel 150 comprises a unitary housing 152 that defines a first chamber or amplification well 154 which has loaded in it an amplification pellet or dried reagent mix 16 for the denaturation step in the TMA process. The amplification well 154 is separated from a second chamber 156 by a heat and moisture isolation barrier 158. The second chamber contains an enzyme plunger or carrier 160 for containing an enzyme pellet 18 for introduction into the amplification well 154 after the fluid sample has been introduced into the amplification well 154 and the denaturation process has been completed. The enzyme plunger 160 has a recessed surface 162 for receiving an implement through the opening at the top of the chamber 156. A foil layer 164 is applied to the top surface of the reaction vessel 150 as shown.

Figure 28:
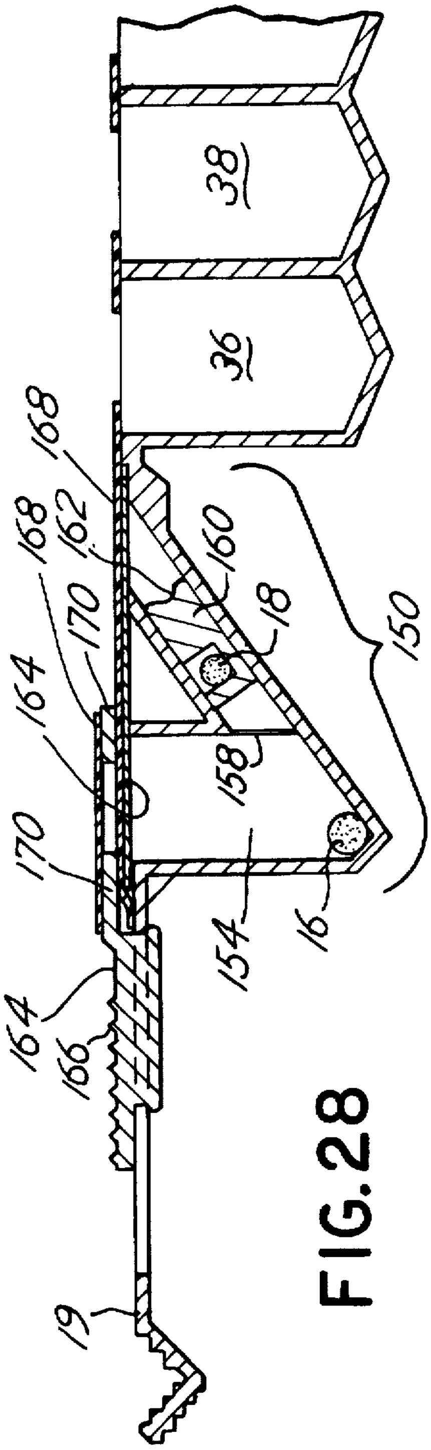
FIG. 28 is a cross-section of a test strip incorporating the embodiment of FIG. 26.

FIG. 28 is a cross-section of a test strip 19 incorporating the embodiment of FIG. 26. The reaction vessel 150 can be manufactured as a stand-alone disposable unit, as suggested in FIGS. 26 or 27, and snapped into place in a test strip as shown in FIG. 28, or the test strip of FIG. 28 may be manufactured with the amplification well of FIG. 31 as an integral part of the test strip 19 itself. In the preferred embodiment, the unit 150 is manufactured as an integral part of the test strip. The test strip 19 has a sliding cover 164 positioned at the end of the test strip 19 comprising a gripping surface 166 and a plastic label 168 carried by first and second mounting structures 170.

Figure 29A:
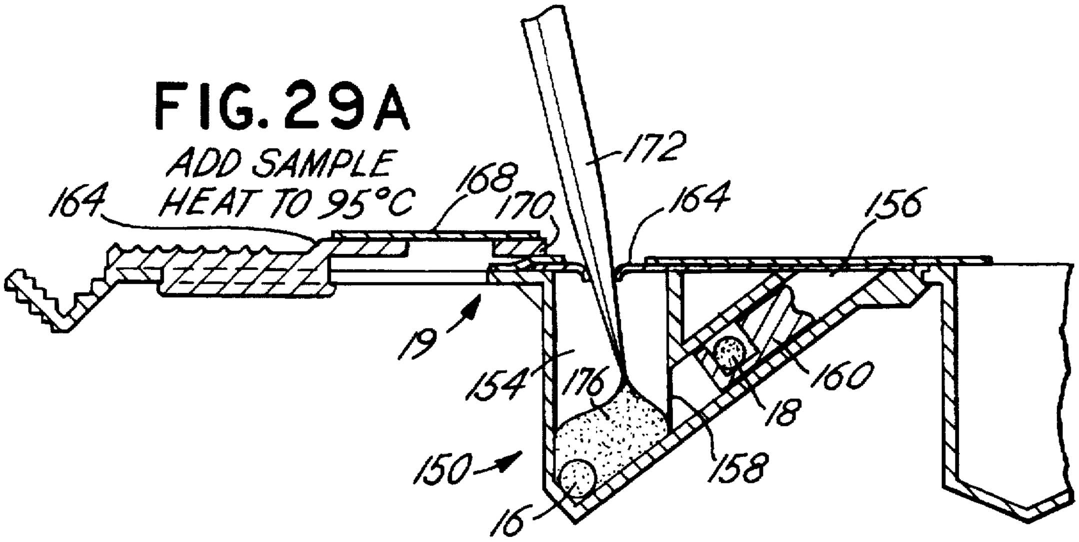
FIGS. 29A–29C show the use of the test strip of FIG. 28.
Figure 29B:
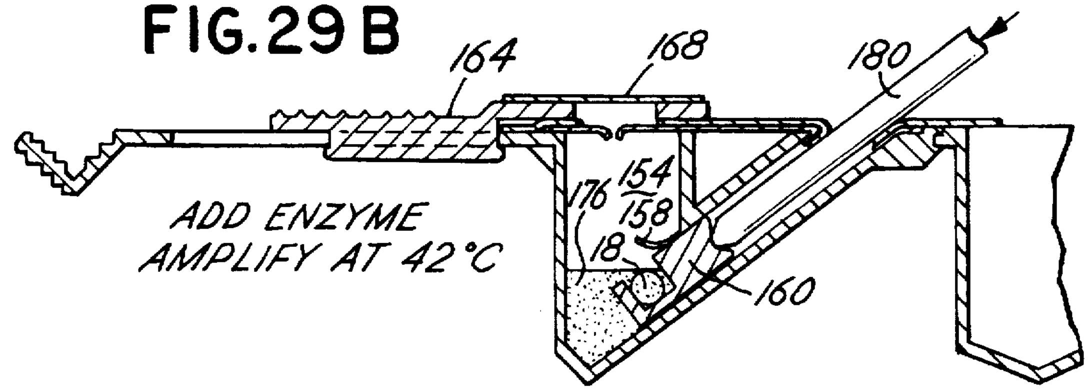
Figure 29C:
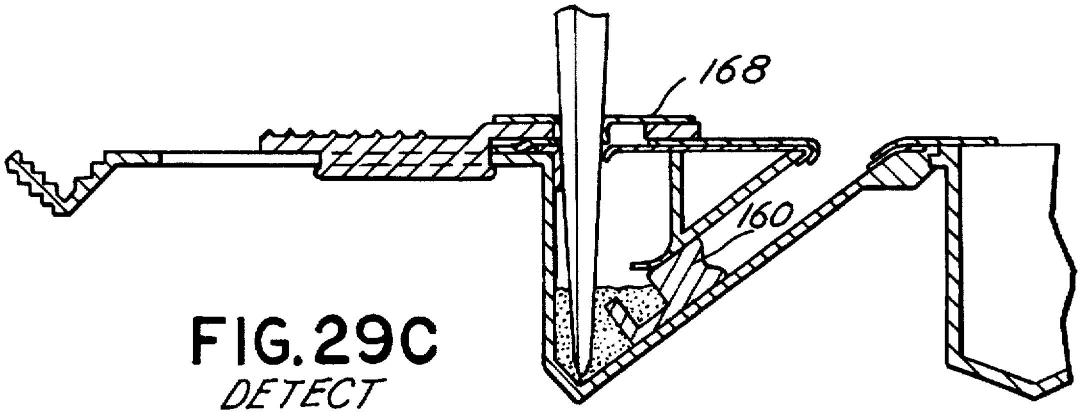

FIGS. 29A–29C show the use of the test strip 19 with the disposable reaction vessel of FIG. 28. In the first step, the sliding cover 164 is pulled back and a pipette 172 is inserted through the foil layer 164 to deposit the fluid sample 176 into the amplification well 154. The pipette 172 is removed and the cover 164 is slid back into place over the amplification well 154 into the position shown in FIG. 29B. The amplification well 154 is heated to 95 degrees C. to subject the fluid sample 176 to denaturation with the aid of the amplification reagent pellet 16. The second chamber 156 containing the enzyme pellet 18 is not subject to the 95 degree C. heating. After the amplification well has cooled down to 42 degrees C., an implement 180 is inserted into the second chamber containing the enzyme carrier 160 and enzyme pellet 18 and placed into contact with the enzyme carrier 160. The implement 180 is moved further in to force the carrier 160 through the heat and moisture isolation barrier 158, thereby adding the enzyme pellet 18 to the amplification well 154. The enzyme carrier 160 blocks the chamber as shown in FIG. 29 C, preventing contamination of the amplification well 154. A cover (not shown) could be slid over the entrance of the second chamber or channel if desired. The amplification well 154 is then maintained at a temperature of 42 degrees C. for roughly one hour for the amplification process to proceed. After the amplification process is complete, a reagent SPR having at least one reaction zone is inserted though a membrane 168 or label as shown in FIG. 29 C, and a portion of the amplified solution is withdrawn into the SPR. The rest of the process proceeds in known fashion.

Dual Chamber Vessel with Piston-actuated Fluid Transfer Embodiment

Figure 30:
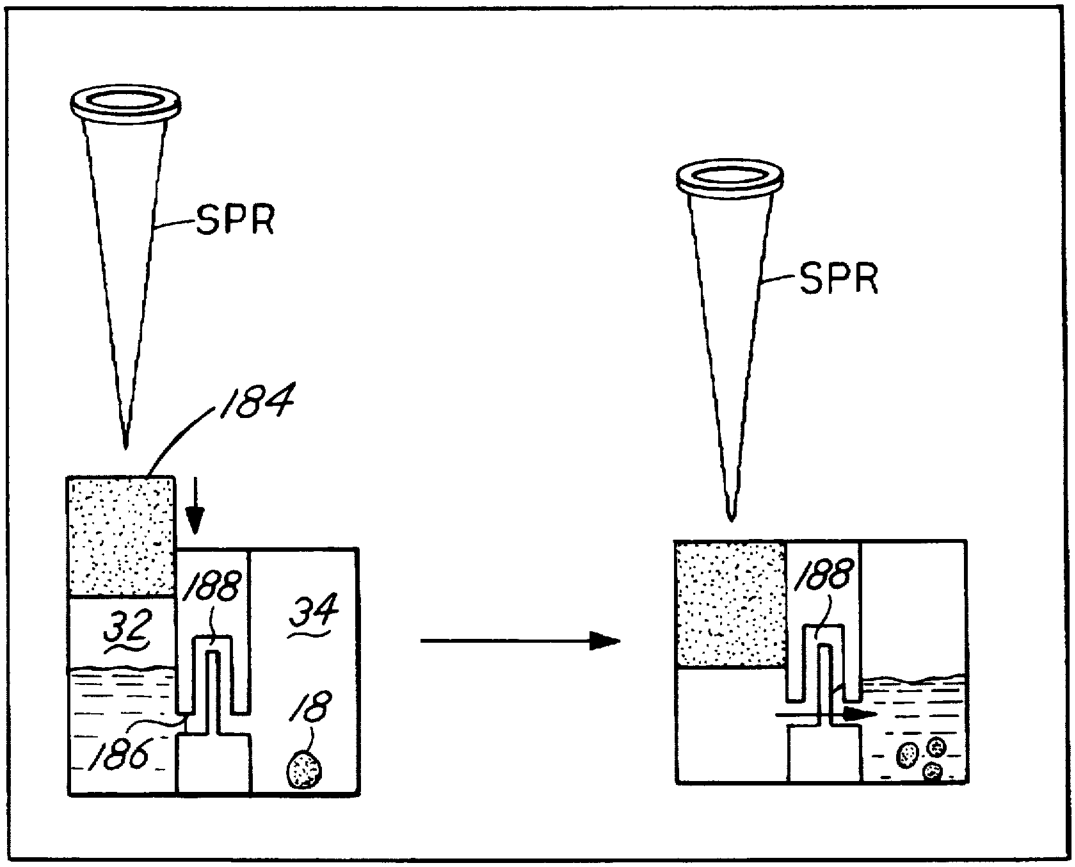
FIG. 30 is a schematic representation of an embodiment of a dual chamber disposable reaction vessel in which a plunger is activated to increase the fluid pressure in the first reaction chamber to break a seal in a fluid channel connecting the first chamber to the second chamber and force a reaction solution in the first chamber into the second chamber for the amplification reaction to take place.

FIG. 30 is a schematic representation of yet another embodiment of a dual chamber disposable reaction vessel 10. The fluid sample is loaded into the first chamber 32 and denaturation and primer annealing steps are performed in the first chamber 32, with the aid of an amplification mix reagent loaded into the first chamber. After the first chamber has cooled to 42 degrees C., a piston mechanism 184 is applied to the first chamber 184 to increase the fluid pressure in the first reaction chamber to break a seal 186 in a fluid channel 188 connecting the first chamber 32 to the second chamber 34. The fluid sample is forced from the first chamber 32 into the second chamber 34. The second chamber is loaded with the enzyme pellet 18. The amplification reaction takes place in the second chamber 34 at a temperature of 42 degrees C. The piston 184 may be incorporated as a cap structure to the reaction vessel 10 and which is depressed by a SPR, as shown, or a separate piston could be used to force the fluid from the first chamber 32 into the second chamber 34.

Amplification Station

Figure 31:
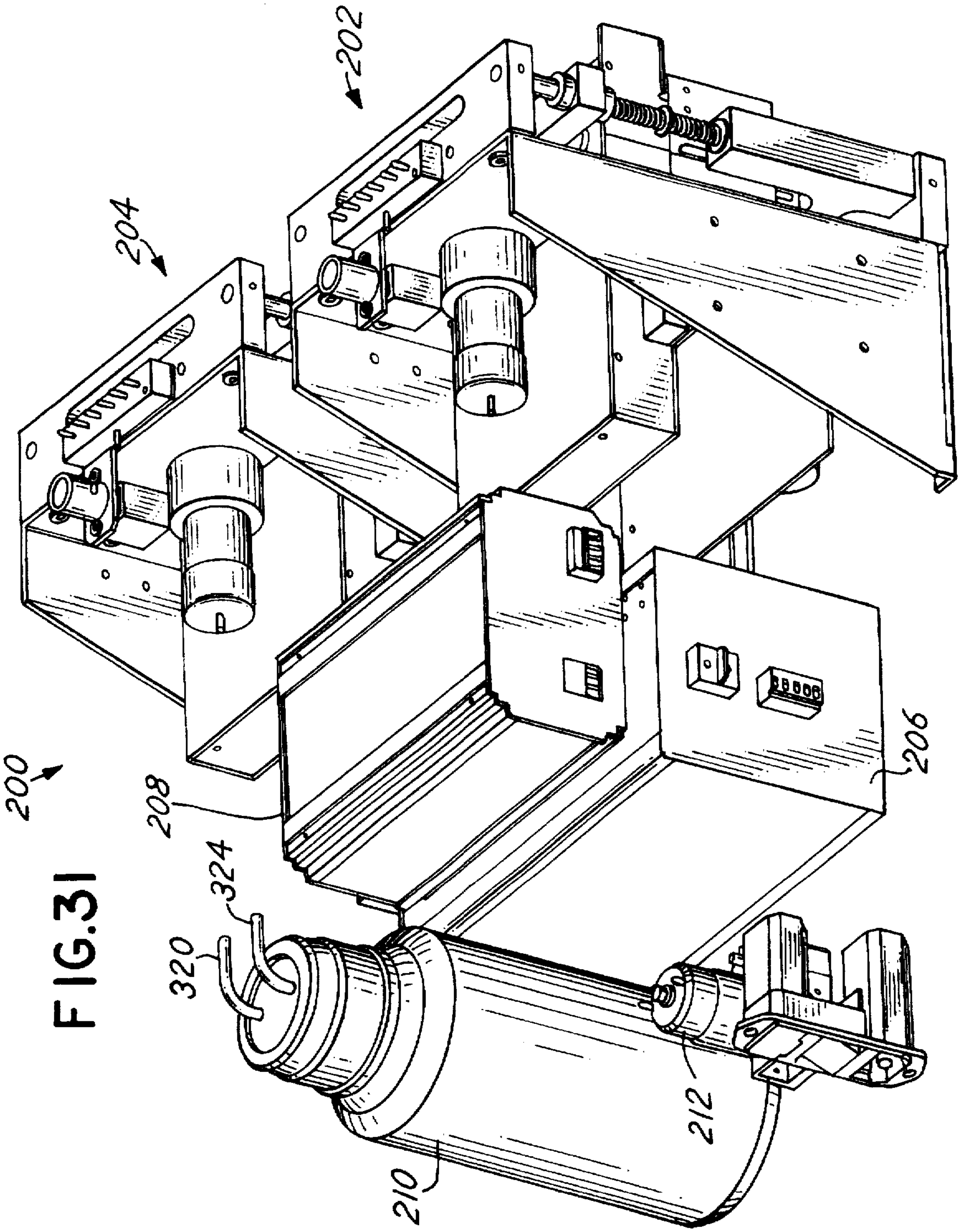
FIG. 31 is a perspective view of a stand-alone amplification processing station for the test strips having the dual chamber reaction vessels in accordance with a presently preferred form of the invention.

FIG. 31 is a perspective view of a stand-alone amplification reaction processing system 200 for the test strips 19 (see, e.g., FIG. 5) having the dual chamber reaction vessels in accordance with a presently preferred form of the invention. The system 200 consists of two identical amplification stations 202 and 204, a power supply module 206, a control circuitry module 208, a vacuum tank 210 and connectors 212 for the power supply module 206. The tank 210 has hoses 320 and 324 for providing vacuum to amplification stations 202 and 204 and ultimately to a plurality of vacuum probes (one per strip) in the manner described above for facilitating transfer of fluid from the first chamber to the second chamber. The vacuum subsystem is described below in conjunction with FIG. 39.

The amplification stations 202 and 204 each have a tray for receiving at least one of the strips 19 of FIG. 5 (in the illustrated embodiment up to 6 strips) and associated temperature control, vacuum and valve activation subsystems for heating the reaction wells of the strip to the proper temperatures, effectuating a transferring of fluid from the first chamber in the dual chamber reaction wells to the second chamber, and activating a valve such as a thimble valve in the embodiment of FIG. 22 to open the fluid channel to allow the fluid to flow between the two chambers.

The stations 202 and 204 are designed as stand alone amplification stations for performing the amplification reaction in an automated manner after the patient or clinical sample has been added to the first chamber of the dual chamber reaction vessel described above. The processing of the strips after the reaction is completed with a SPR takes place in a separate machine, such as the commercially available VIDAS instrument. Specifically, after the strips have been placed in the stations 202 and 204 and the reaction run in the stations, the strips are removed from the stations 202 and 204 and placed into a is VIDAS instrument for subsequent processing and analysis in known fashion.

The entire system 200 is under microprocessor control by an amplification system interface board (not shown in FIG. 31). The control system is shown in block diagram form in FIG. 38 and will be described later.

Figure 32:
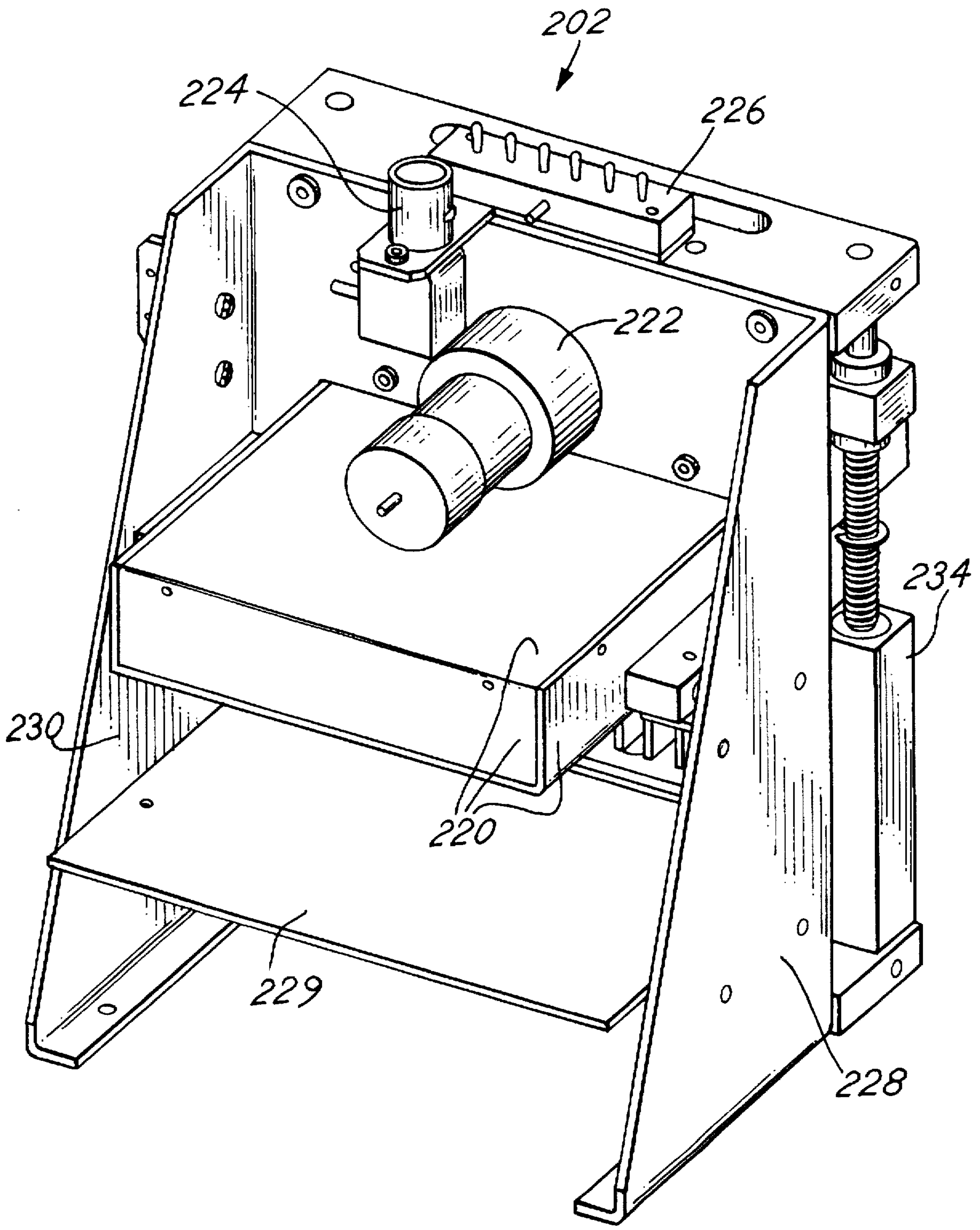
FIG. 32 is a perspective view of one of the amplification modules of FIG. 31, as seen from the rear of the module.
Figure 33:
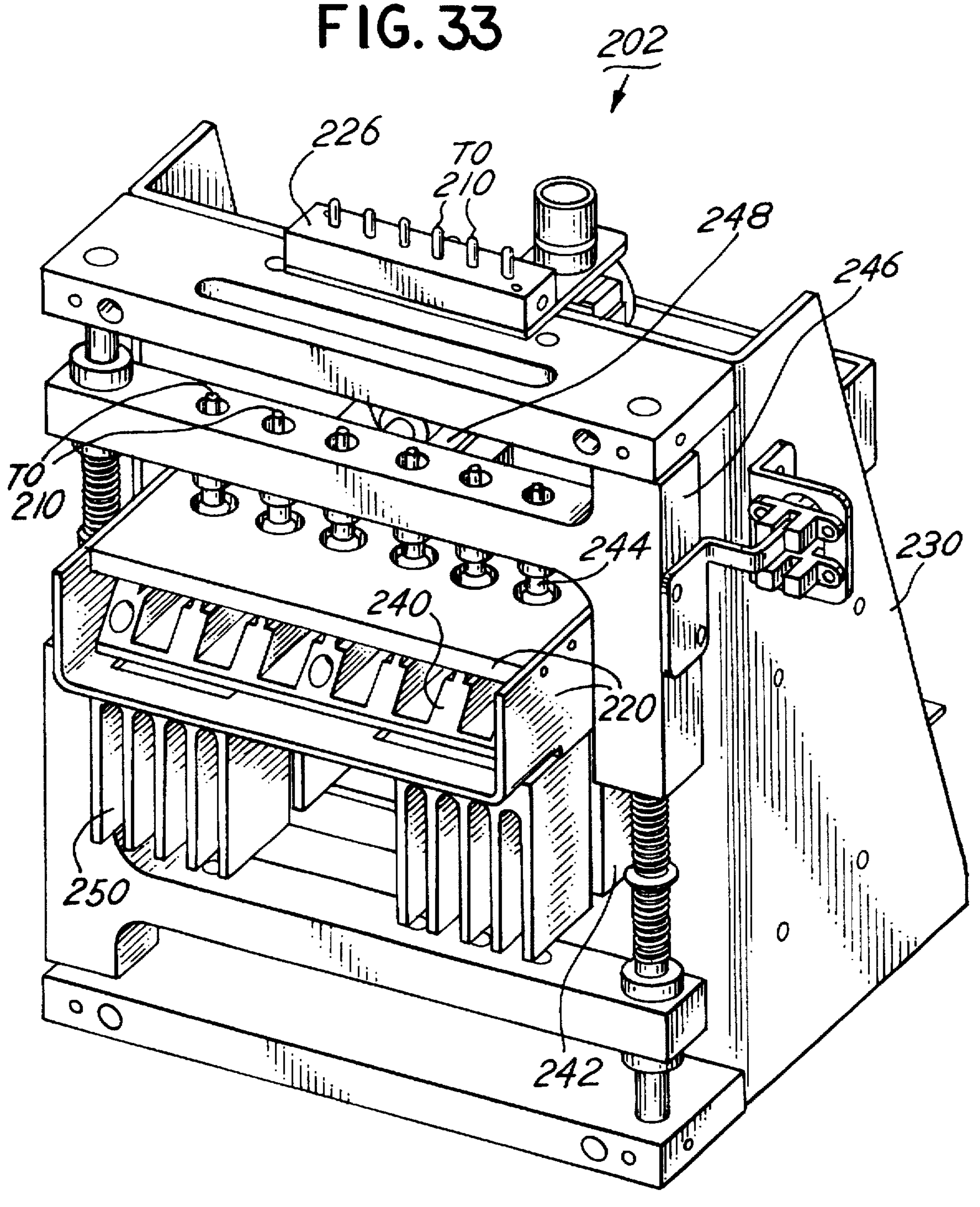
FIG. 33 is a perspective view of the front of the module of FIG. 32.

Referring now to FIG. 32, one of the amplification stations 202 is shown in a 20 perspective view. The other amplification station is of identical design and construction. FIG. 33 is a perspective view of the front of the station 202 of FIG. 31.

Referring to these figures, the station includes a vacuum probe slide motor 222 and vacuum probes slide cam wheel 246 that operate to slide a set of vacuum probes 244 (shown in FIG. 33) for the thimble valves of FIG. 21 up and down relative to a vacuum probes slide 246 to open the thimble valves (reference 140 in the embodiment of FIGS. 21–23) and apply vacuum so as to draw the fluid from the first chamber of the reaction vessel 10 (e.g., FIG. 21) to the second chamber. The vacuum probes 244 reciprocate within annular recesses provided in the vacuum probes slide 246. The vacuum probes 244 are positioned in registry with the intermediate chamber 70 in the embodiment of FIG. 22, or in registry with the vacuum port 80 in the embodiment of FIG. 11.

For an embodiment in which the strips are constructed in the manner of FIGS. 5–12, the vacuum probe 244 would incorporate a suitable pin structure (not shown) immediately adjacent the shaft of the vacuum probe 244 that would operate the plunger 56 of FIG. 12 to open the intermediate chamber 70 when the vacuum probe 244 is lowered onto the vacuum port. Obviously, proper registry of the pin structure and vacuum probe 244 with corresponding structure in the test strip as installed on the tray needs to be observed.

The station includes side walls 228 and 230 that provide a frame for the station 202. Tray controller board 229 is mounted between the side walls 228 and 230. The electronics module for the station 202 is installed on the tray controller board 229.

A set of tray thermal insulation covers 220 are part of a thermal subsystem and are provided to envelop a tray 240 (FIG. 33) that receives one or more of the test strips. The insulation covers 220 help maintain the temperature of the tray 240 at the proper temperatures. The thermal subsystem also includes a 42 degree C. Peltier heat sink 242, a portion of which is positioned adjacent to the second chamber in the dual chamber reaction vessel in the test strip to maintain that chamber at the proper temperature for the enzymatic amplification reaction. A 95 degree C. heat sink 250 is provided for the front of the tray 240 for maintaining the first chamber of the reaction well in the test strip at the denaturation temperature.

Figure 34:
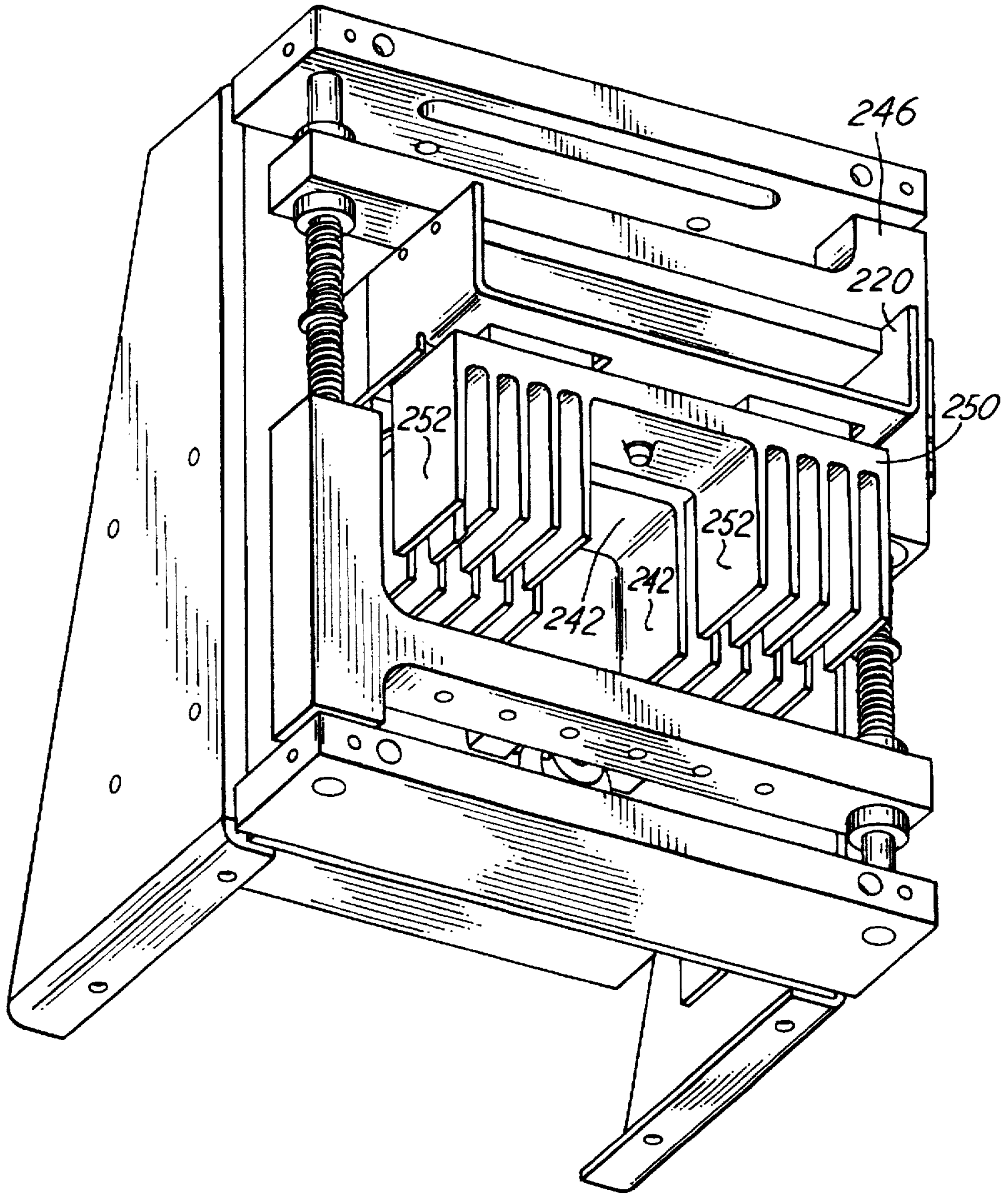
FIG. 34 is another perspective view of the module of FIG. 33.

FIG. 34 is another perspective view of the module of FIG. 33, showing the 95 degree C. heat sink 250 and a set of fins 252 dissipating heat. Note that the 95 degree C. heat sink 250 is positioned to the front of and slightly below the tray 240. The 42 degree C. heat sink 242 is positioned behind the heat sink 250.

Figure 35:
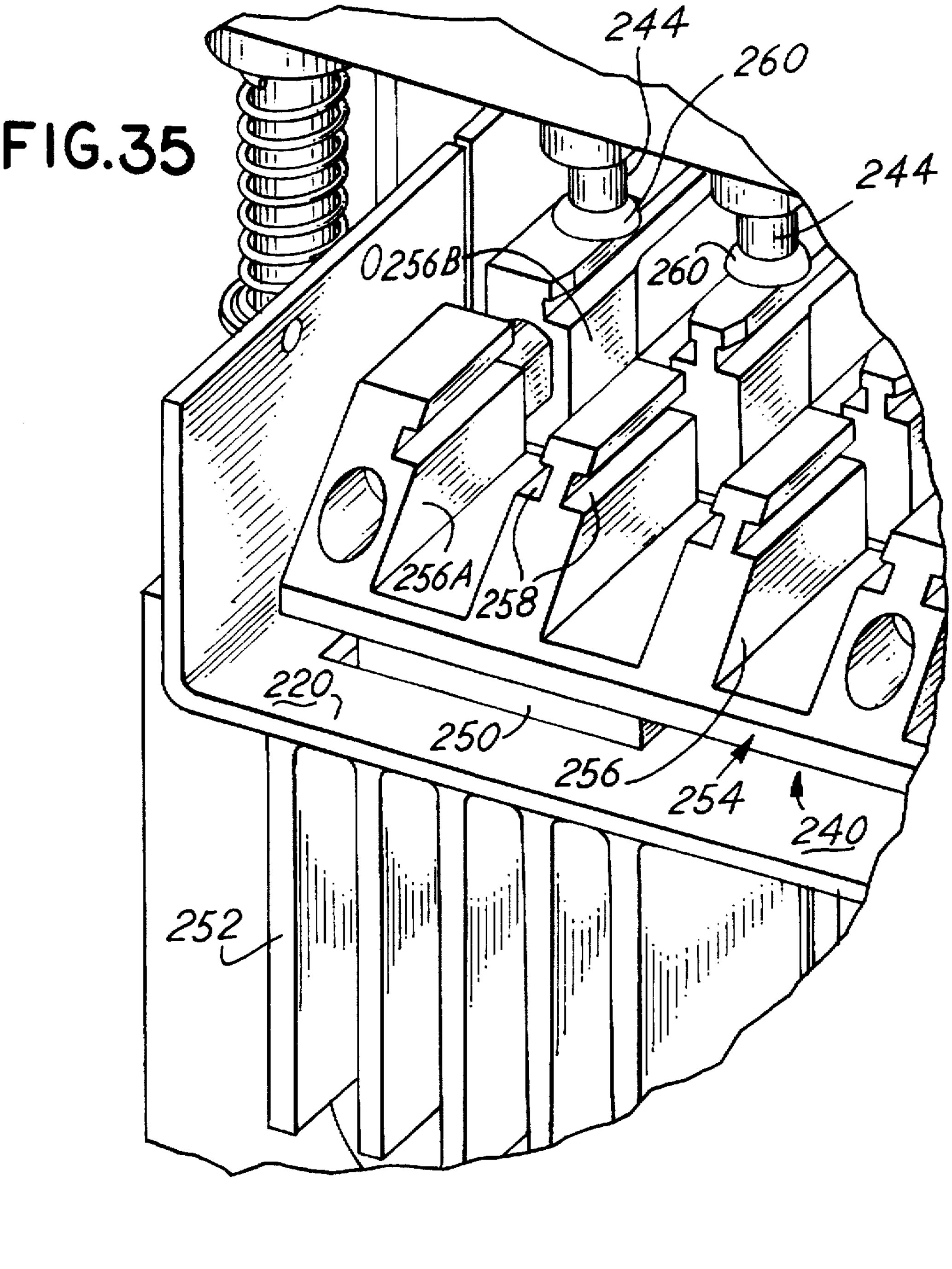
FIG. 35 is a detailed perspective view of a portion of the test strip holder and 95 degree C. Peltier heating subsystems of the module of FIGS. 32–34.

FIG. 35 is a detailed perspective view of a portion of the tray 240 that holds the test strips (not shown) as seen from above. The tray 240 includes a front portion having a base 254, and a plurality of discontinuous raised parallel ridge structures 256 with recessed slots 258 for receiving the test strips. The base of the front 254 of the tray 240 is in contact with the 95 degree C. heat sink 250. The side walls of the parallel raised ridges 256 at positions 256A and 256B are placed as close as possible to the first and second chambers of the reaction vessel 10 of FIG. 1 so as to reduce thermal resistance. The base of the rear of the tray 240 is in contact with a 42 degree C. Peltier heat sink, as best seen in FIG. 34. The portion 256B of the raised ridge for the rear of the tray is physically isolated from portion 256A for the front of the tray, and portion 256B is in contact with the 42 degree C. heat sink so as to keep the second chamber of the reaction vessel in the test strip at the proper temperature.

Still referring to FIG. 35, each of the vacuum probes 244 include a rubber gasket 260. When the vacuum probes 244 are lowered by the vacuum probe motor 222 (FIG. 32) the gaskets 260 are positioned on the film covering the upper surface of the test strip surrounding the vacuum port in the dual chamber reaction vessel so as to make a tight seal and permit vacuum to be drawn on the second chamber.

Figure 36:
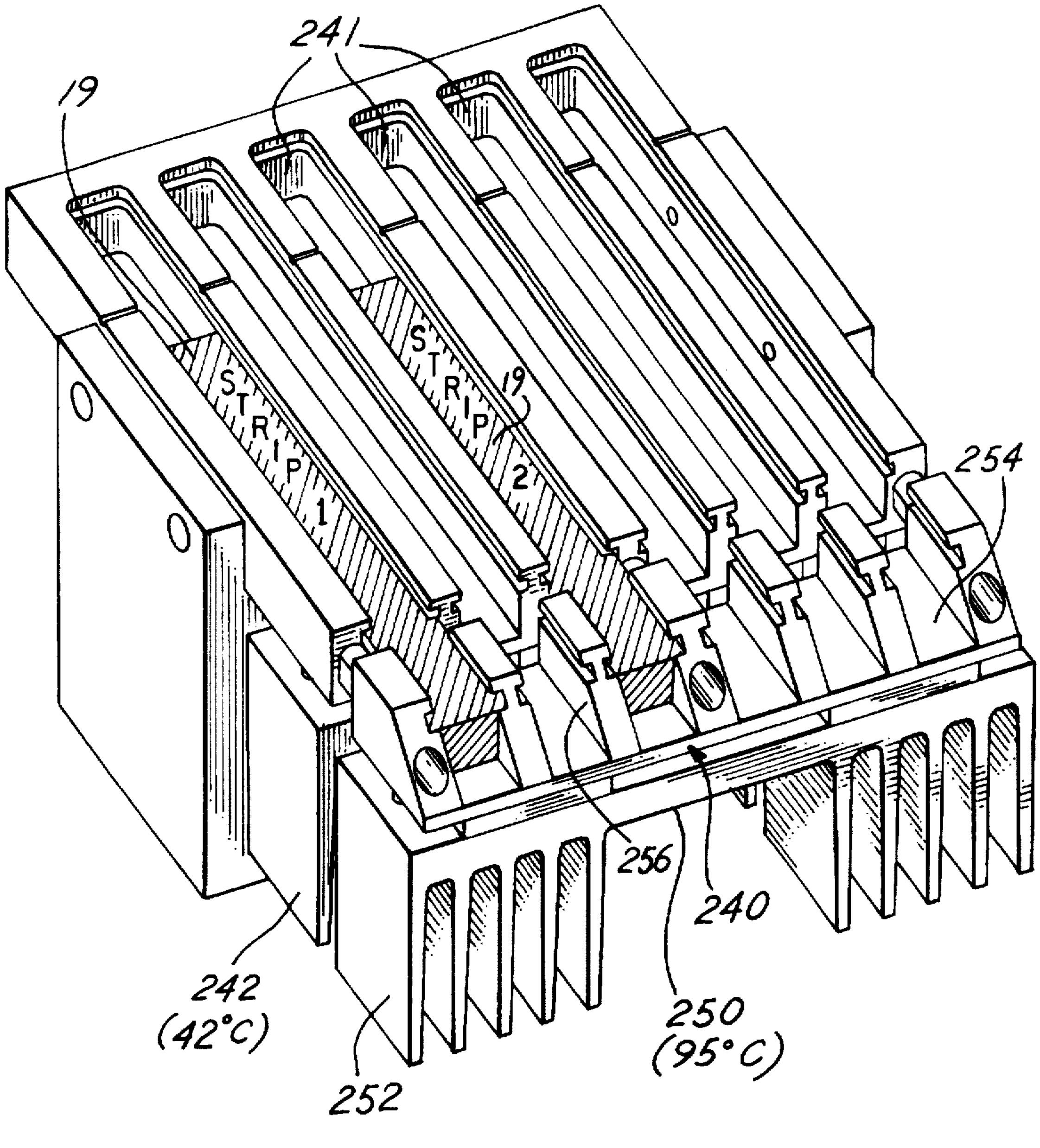
FIG. 36 is an isolated perspective view of the test strip holder of FIG. 35, showing two test strips in accordance with FIG. 5 installed in the test strip holder.

FIG. 36 is an isolated perspective view of the test strip holder or tray 240 of FIG. 35, showing two test strips 19 in accordance with FIG. 5 installed in the tray 240. The tray 240 has a plurality of lanes or slots 241 receiving up to 6 test strips 19 for simultaneous processing. FIG. 36 shows the heat sinks 242 and 250 for maintaining the respective portions of the tray 240 and ridges 256 at the proper temperature.

Figure 37:
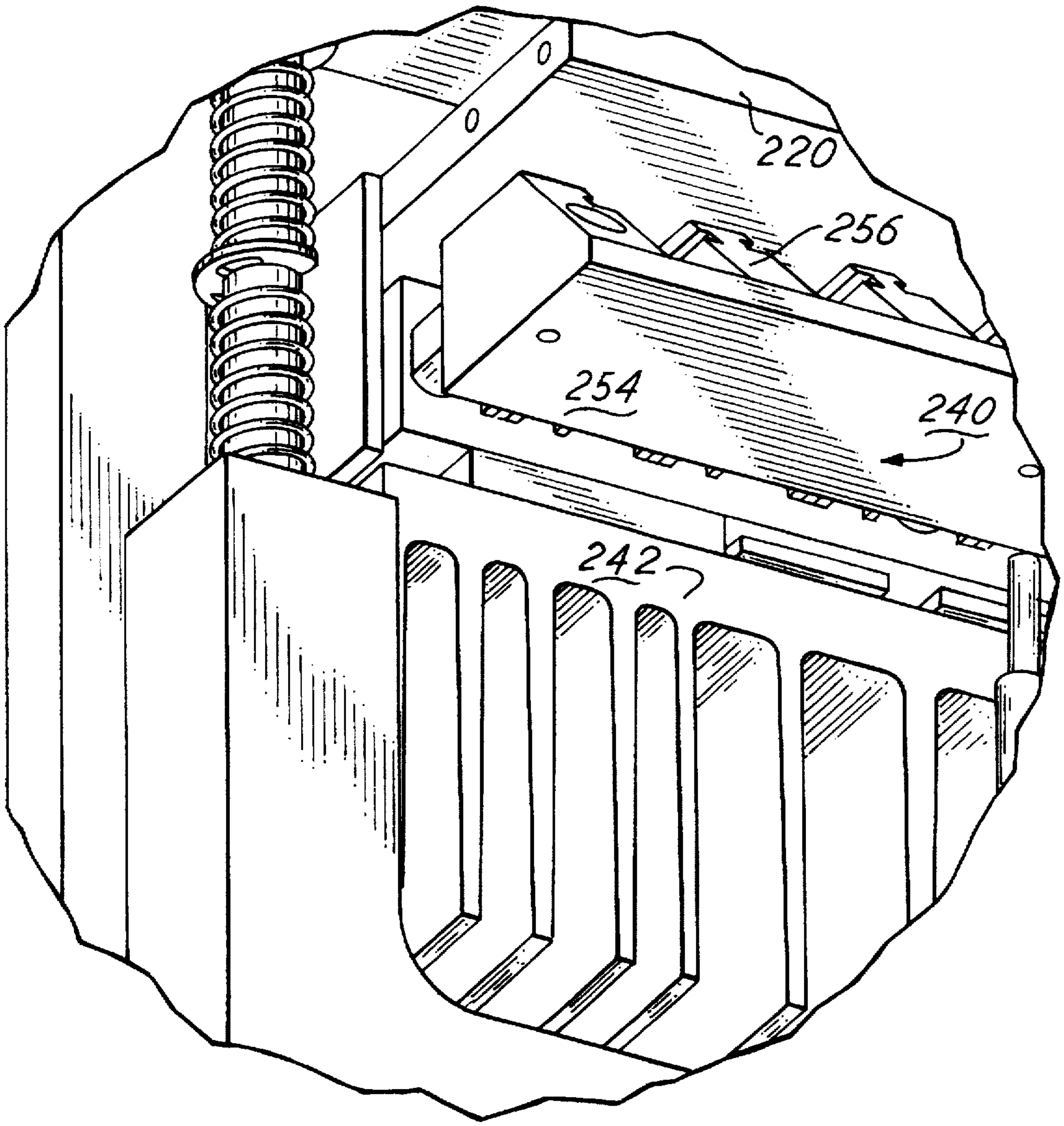
FIG. 37 is a detailed perspective view of the test strip holder or tray of FIG. 33.

FIG. 37 is a detailed perspective view of the test strip holder or tray 240 as seen from below. The 95 degree C. Peltier heat sink which would be below front portion 254 has been removed in order to better illustrate the rear heat sink 242 beneath the rear portion of the tray 240.

Figure 38:
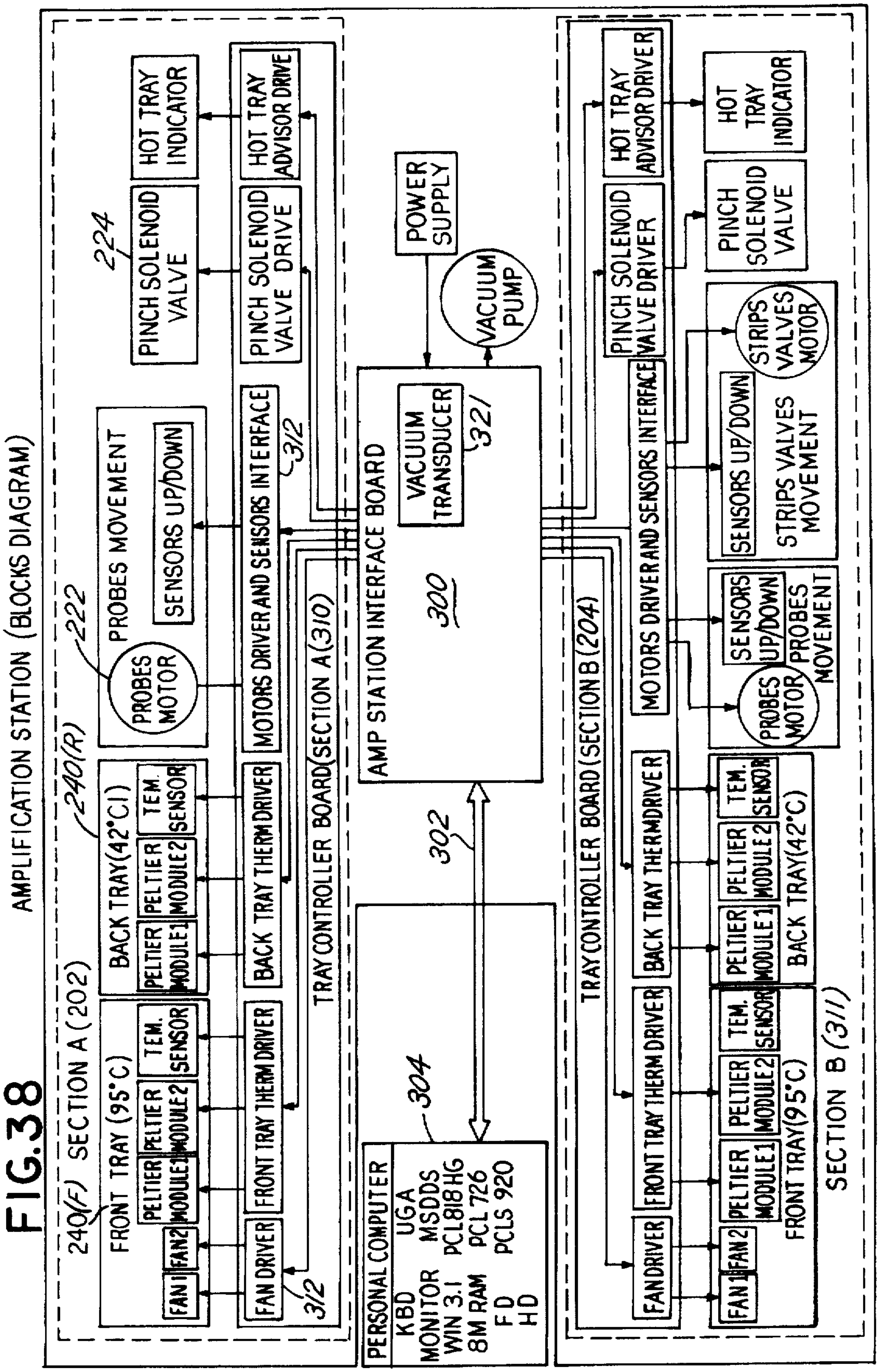
FIG. 38 is a block diagram of the electronics of the amplification processing station of FIG. 33.

FIG. 38 is a block diagram of the electronics and control system of the amplification processing system of FIG. 31. The control system is divided into two boards 310 and 311, section A 310 at the top of the diagram devoted to amplification module or station 202 and the other board 311 (section B) devoted to the other module 204. The two boards 310 and 311 are identical and only the top section 310 will be discussed. The two boards 310 and 311 are connected to an amplification station interface board 300.

The interface board 300 communicates with a stand alone personal computer 304 via a high speed data bus 302. The personal computer 304 is a conventional IBM compatible computer with hard disk drive, video monitor, etc. In a preferred embodiment, the stations 202 and 204 are under control by the interface board 300.

The board 310 for station 202 controls the front tray 240 which is maintained at a temperature of 95 degrees C. by two Peltier heat sink modules, a pair of fans and a temperature sensor incorporated into the front portion 254 of the tray 240, all of which are conventional. The back of the tray is maintained at a temperature of 42 degrees C. by two Peltier modules and a temperature sensor. The movement of the vacuum probes 244 is controlled by the probes motor 222. Position sensors are provided to provide input signals to the tray controller board as to the position of the vacuum probes 244. The tray controller board 310 includes a set of drivers 312 for the active and passive components of the system which receive data from the temperature and position sensors and issue commands to the active components, i.e., motors, fans, Peltier modules, etc. The drivers are responsive to commands from the amplification interface board 300. The interface board also issues commands to the vacuum pump for the vacuum subsystem, as shown.

Figure 39:
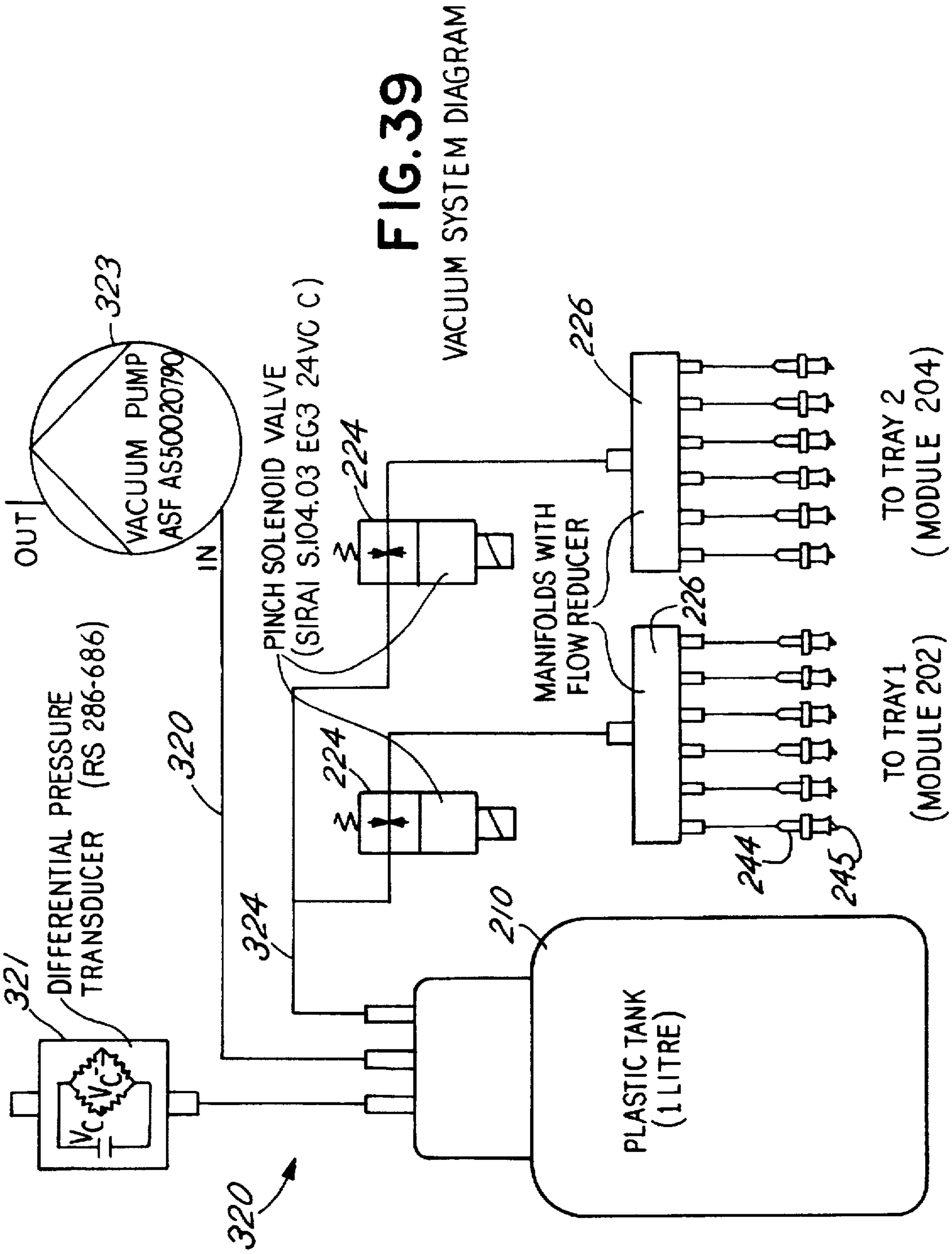
FIG. 39 is a diagram of the vacuum subsystem for the amplification processing station of FIG. 31.

FIG. 39 is a diagram of the vacuum subsystem 320 for the amplification processing stations 202 and 204 of FIG. 31. The subsystem includes a 1 liter reinforced plastic vacuum tank 210 which is connected via an inlet line 322 to a vacuum pump 323 for generating a vacuum in the tank 210. A vacuum supply line 324 is provided for providing vacuum to a pair of pinch solenoid valves 224 (see FIG. 32) via supply lines 324A and 324B. These vacuum supply lines 324A and 324B supply vacuum to a manifold 226 distributing the vacuum to the vacuum probes 244. Note the pointed tips 245 of the vacuum probes 244 for piercing the film or membrane 64 (FIG. 11) covering the strip 19. The vacuum system 320 also includes a differential pressure transducer 321 for monitoring the presence of vacuum in the tank 210. The transducer 321 supplies pressure signals to the interface board 300 of FIG. 38.

Figure 40:
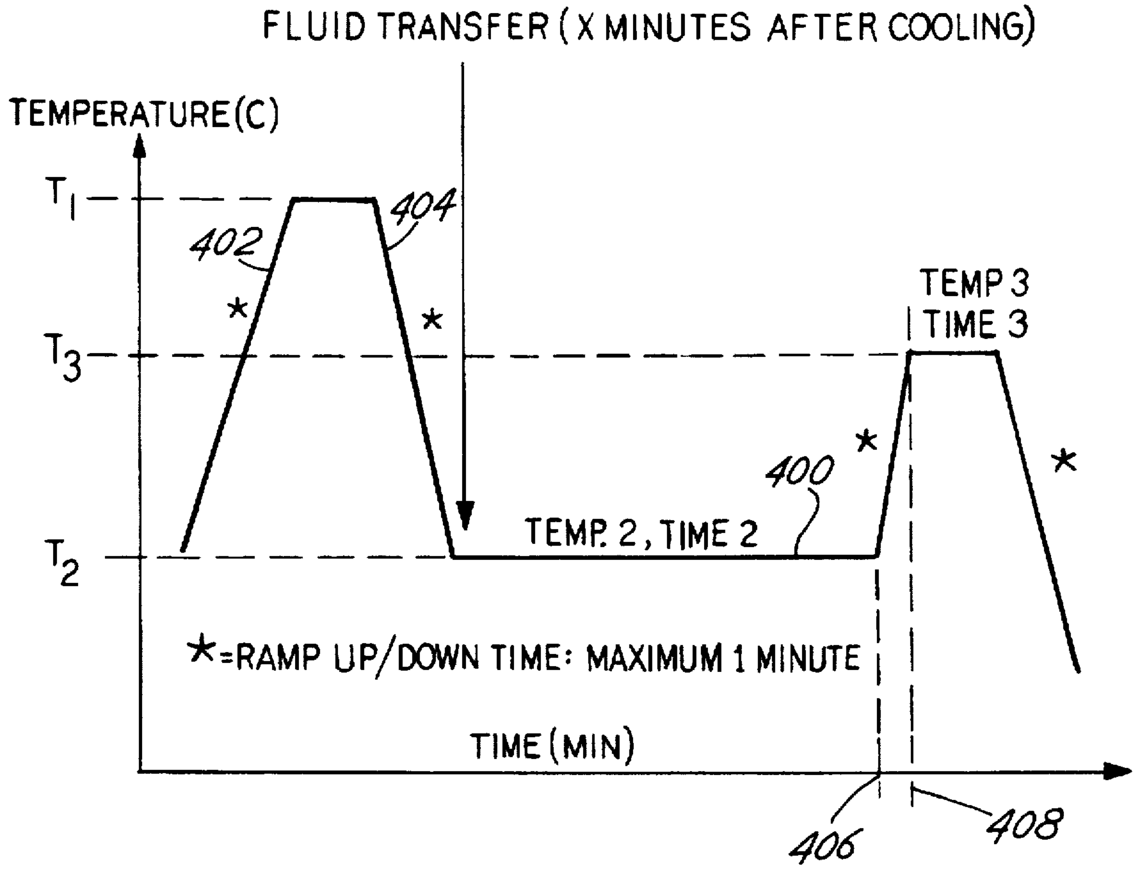
FIG. 40 is a graph of the thermal cycle of the station of FIG. 31.

FIG. 40 is a representative graph of the thermal cycle profile of the station of FIG. 31. As indicated in line 400, after an initial ramp up 402 in the temperature lasting less than a minute, a first temperature T1 is reached (e.g., a denaturation temperature) which is maintained for a predetermined time period, such as 5–10 minutes, at which time a reaction occurs in the first chamber of the reaction vessel. Thereafter, a ramp down of temperature as indicated at 404 occurs and the temperature of the reaction solution in the first chamber of the reaction vessel 10 cools to temperature T2. After a designated amount of time after cooling to temperature T2, e.g., 42 degrees C., a fluid transfer occurs in which the solution in the first chamber is conveyed to the second chamber. Temperature T2 is maintained for an appropriate amount of time for the reaction of interest, such as one hour. At time 406, the temperature is raised rapidly to a temperature T3 of ≧65 degrees C. to stop the amplification reaction. For a TMA reaction, it is important that the ramp up time from time 406 to time 408 is brief, that is, less than 2 minutes and preferably less than one minute. Preferably, all the ramp up and ramp down of temperatures occur in less than a minute.

Presently preferred techniques for preparation of the enzyme for the second chamber in pellet form is set forth in the patent application of Brian W. Kluttz filed concurrently, Ser. No. 08/850,171, which is incorporated by reference herein.

While presently preferred embodiments of the invention have been described herein, persons of skill in the art will appreciate that various modifications and changes may be made without departure from the true scope and spirit of the invention. For example, the novel reaction vessels and test strips can be used in other reactions besides isothermal amplification reactions such as TMA. The invention is believed to be suitable for many isothermal reactions, other enzymatic reactions, and reactions requiring differential heating and containment. For example, the reference to "denaturation and cooling", while specifically applicable to the TMA reaction, can be considered only one possible species of a heat differential step. Further, the spatial and temperature isolation of the amplification enzyme in the second chamber is considered one example of spatial isolation of a heat labile reagent. The invention is fully capable of being used in other types of reactions besides TMA reactions. This true scope and spirit is defined by the claims, to be interpreted in light of the foregoing.

We claim:

1. A dual chamber reaction vessel for a nucleic acid amplification reaction, the vessel comprising:
   - a first chamber for receiving a fluid sample, said first chamber loaded with an amplification reagent(s);
   - a second chamber physically isolated from said first chamber;
   - an enzyme(s) for said reaction either in said second chamber or in fluid communication with said second chamber; and
   - a fluid channel connecting said first chamber to said second chamber.

2. The dual chamber reaction vessel of claim 1, further comprising a means for selectively opening said fluid channel to allow a fluid to pass from said first chamber into said second chamber.

3. The dual chamber reaction vessel of claim 2, wherein said means for selectively opening said fluid channel comprises a breakable seal.

4. The dual chamber reaction vessel of claim 2, wherein said means for selectively opening said fluid channel comprises a valve.

5. The dual chamber reaction vessel of claim 3, wherein said means for selectively opening said fluid channel comprises a means for creating fluid pressure in said sample fluid so as to break said seal and enable fluid to flow from said first chamber through said fluid channel into said second chamber.

6. The dual chamber reaction vessel of claim 3, wherein said means for selectively opening said fluid channel comprises a plunger reciprocable within said vessel from a first position to a second position, said plunger in said second position operable to cut said seal and thereby open said fluid channel.

7. The dual chamber reaction vessel of claim 4, wherein said valve comprises a thimble valve.

8. The dual chamber reaction vessel of claim 1, wherein said vessel further comprises a vacuum port in fluid communication with said second chamber, whereby the application of vacuum to said vacuum port draws said fluid sample from said first chamber into said second chamber.

9. A reaction vessel for a nucleic acid amplification reaction, comprising:

- an amplification well;
- a channel separated from said amplification well by a heat and moisture barrier;
- a carrier in said channel carrying an amplification enzyme;
- wherein said carrier is moveable within said channel such that said carrier may be moved through said heat and moisture barrier to deliver said enzyme to said amplification well.

10. A two-piece disposable reaction vessel, comprising:

- a first piece comprising a first chamber containing an amplification reagent;
- a second piece comprising a second chamber containing an amplification enzyme;
- said first and second pieces constructed so as permit said first and second pieces to be securely joined into an dual chamber reaction vessel such that a fluid sample in said first piece may pass into said second chamber.

11. A test strip incorporating the reaction vessel of any one of claims 1–10.

12. In a test strip for a nucleic acid amplification reaction comprising a body portion defining a plurality of wells arranged in a row and having a first end and a second end, said second end having a cuvette for conducting an optical analysis of a sample, the improvement comprising:

- providing an aperture in said body portion adjacent to said first end of said test strip for receiving a disposable amplification reaction vessel.

13. The improvement of claim 12, wherein said disposable reaction vessel comprises one of the reaction vessels claimed in one of claims 1–10.

14. A method for conducting a nucleic acid amplification reaction, comprising the steps of:

- providing a dual chamber reaction vessel comprising first and second chambers capable of being placed in fluid communication with each other, said dual chamber reaction vessel loaded with an amplification reagent(s) into said first chamber and an amplification enzyme(s) in said second chamber;
- sealing said first and second chambers with said amplification reagent(s) and amplification enzyme(s) from the environment with a sealing means after loading said amplification reagent(s) and amplification enzyme(s) in said dual chamber reaction vessel;
- and, at the time of use of said dual chamber reaction vessel;
- opening said sealing means with an implement and loading a sample into said first chamber;
- heating said first chamber and said sample to a first relatively high temperature while maintaining said second chamber at a second relatively low temperature;
- cooling said first chamber and a solution of said sample and said amplification reagent(s) from said first relatively high temperature;
- thereafter passing said solution from said first chamber to said second chamber; and
- amplifying said solution in said second chamber by said amplification enzyme(s).

15. The method of claim 14, further comprising the step of applying vacuum to said second chamber so as to draw said solution through said fluid channel from said first chamber to said second chamber.

16. A method for conducting a nucleic acid amplification reaction, comprising the steps of:

- providing a reaction vessel comprising an amplification chamber and a second chamber separated from said amplification chamber by a heat and moisture barrier;
- loading an amplification reagent(s) into said amplification chamber and an amplification enzyme(s) in said second chamber;
- loading a sample into said amplification chamber;
- heating said first chamber and said sample to a first relatively high temperature greater than or equal to 65 degrees C. while maintaining said enzyme in said second chamber at a relatively cooler second temperature;
- cooling said first chamber and a solution of said sample and said amplification reagent(s); and
- thereafter introducing said amplification enzyme(s) into said amplification chamber by forcing said enzyme(s) through said heat and moisture barrier into said amplification chamber; and
- amplifying said solution in said amplification chamber.

17. A nucleic acid amplification station for a test strip, said test strip comprising a dual chamber reaction vessel comprising a first chamber and a second chamber, the station comprising:

- a tray for at least one test strip, said tray comprising a first portion and a second portion positioned adjacent to first and second chambers of said dual chamber reaction vessel, respectively;
- a temperature control subsystem for said tray maintaining said first and second portions of said tray at first and second different amplification reaction temperatures so as to maintain said first and second chambers at said first and second amplification reaction temperatures, respectively;
- a fluid conduit opening mechanism for opening a fluid conduit in said dual chamber reaction vessel to thereby establish fluid communication between said first chamber and said second chamber; and
- a vacuum subsystem including a vacuum probe, said test strip and vacuum probe reciprocable relative to each other, said vacuum probe cooperating with said reaction wells in said test strip for transferring a fluid sample from said first chamber to said second chamber via said fluid conduit.

18. The station of claim 17, wherein said fluid conduit opening mechanism comprises a pin for said test strip reciprocable with said vacuum probe relative to said test strip.

19. The station of claim 17, wherein said vacuum probe comprises a tip portion, and wherein said fluid conduit opening mechanism comprises said tip portion of said vacuum probe.

20. The station of claim 17, wherein said temperature control subsystem further comprises a first heat sink for heating said first portion of said test strip to said first temperature and a second heat sink isolated from said first heat sink for maintaining said second portion of said test strip at a second temperature.

21. The station of claim 17 wherein said tray comprises a base and a plurality of raised ridges defining slots for receiving a plurality of test strips.

22. The station of claim 21, wherein said raised ridges are discontinuous, with a first portion of said raised ridges in contact with a first heat sink and a second portion of said raised ridges in contact with a second heat sink.

23. A test strip incorporating the reaction vessel of any one of claims 1–10, wherein said test strip further comprises an optical cuvette for conducting an optical analysis of a sample.

24. A nucleic acid amplification station for a test strip, said test strip comprising a dual chamber reaction vessel comprising a first chamber and a second chamber, the station comprising:

a tray for at least one test strip, said tray comprising a first portion and a second portion positioned adjacent to first and second chambers of said dual chamber reaction vessel, respectively;

a temperature control subsystem for said tray maintaining said first and second portions of said tray at first and second different amplification reaction temperatures so as to maintain said first and second chambers at said first and second amplification reaction temperatures, respectively, during processing of said test strip; and a fluid conduit opening mechanism for opening a fluid conduit in said dual chamber reaction vessel to thereby establish fluid communication between said first chamber and said second chamber.

25. A method for conducting a nucleic acid amplification reaction, comprising the steps of:

providing a dual chamber reaction vessel comprising first and second chambers capable of being placed in fluid communication with each other, said dual chamber reaction vessel loaded with an amplification reagent(s) into said first chamber and an amplification enzyme(s) in said second chamber;

sealing said first and second chambers with said amplification reagent(s) and amplification enzyme(s) from the environment with a sealing means after loading said amplification reagent(s) and amplification enzyme(s) in said dual chamber reaction vessel;

and, at the time of use of said dual chamber reaction vessel;

opening said membrane with an implement and loading a sample into said first chamber;

heating said first chamber and said sample to a first relatively high temperature while maintaining said second chamber at a second relatively low temperature;

cooling said first chamber and a solution of said sample and said amplification reagent(s) from said first relatively high temperature;

thereafter introducing the contents of said second chamber into said first chamber; and amplifying said sample in first chamber with said amplification enzyme(s).

* * * * *